(12) United States Patent
Ashton et al.

(10) Patent No.: US 11,390,846 B2
(45) Date of Patent: Jul. 19, 2022

(54) METHODS FOR CONTROLLED INDUCTION OF 3D CYLINDRICAL NEUROEPITHELIAL TUBES

(71) Applicant: Wisconsin Alumni Research Foundation, Madison, WI (US)

(72) Inventors: Randolph Scott Ashton, Madison, WI (US); Carlos Ruben Marti-Figueroa, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 378 days.

(21) Appl. No.: 16/654,952

(22) Filed: Oct. 16, 2019

(65) Prior Publication Data

US 2020/0115677 A1   Apr. 16, 2020

Related U.S. Application Data

(60) Provisional application No. 62/746,373, filed on Oct. 16, 2018.

(51) Int. Cl.
*C12N 5/079* (2010.01)
*C12N 5/00* (2006.01)

(52) U.S. Cl.
CPC ......... *C12N 5/0618* (2013.01); *C12N 5/0062* (2013.01); *C12N 2500/05* (2013.01); *C12N 2500/32* (2013.01); *C12N 2500/38* (2013.01); *C12N 2501/33* (2013.01); *C12N 2501/999* (2013.01); *C12N 2506/02* (2013.01); *C12N 2506/03* (2013.01); *C12N 2506/45* (2013.01); *C12N 2513/00* (2013.01); *C12N 2533/18* (2013.01); *C12N 2533/30* (2013.01); *C12N 2533/74* (2013.01); *C12N 2537/10* (2013.01)

(58) Field of Classification Search
CPC ............... C12N 5/0618; C12N 5/0062; C12N 2500/05; C12N 2500/32; C12N 2500/38; C12N 2501/33; C12N 2501/999; C12N 2506/02; C12N 2506/03; C12N 2506/45; C12N 2513/00; C12N 2533/74; C12N 2537/10

See application file for complete search history.

(56) References Cited

U.S. PATENT DOCUMENTS

| | | |
|---|---|---|
| 2014/0134732 A1 | 5/2014 | Ashton |
| 2016/0068806 A1 | 3/2016 | Ashton |
| 2017/0157802 A1* | 6/2017 | Ashton ................ C08J 3/075 |
| 2019/0024046 A1 | 1/2019 | Ashton |

OTHER PUBLICATIONS

Zhu et al., A hollow fiber system for simple generation of human brain organoids. Integrative Biology, vol. 9 (2017) 774. (Year: 2017).*

(Continued)

*Primary Examiner* — Kara D Johnson
(74) *Attorney, Agent, or Firm* — McDonnell Boehnen Hulbert and Berghoff LLP

(57) ABSTRACT

Described herein are methods, compositions, and kits for forming engineered in vitro biomimetic, three-dimensional, tubular organoid structures by directed differentiation of human pluripotent stem cells within tubular channels formed in a hydrogel.

18 Claims, 12 Drawing Sheets
(12 of 12 Drawing Sheet(s) Filed in Color)

(56) References Cited

OTHER PUBLICATIONS

Chen, G., et al. "Chemically defined conditions for human iPSC derivation and culture." Nature methods 8.5 (2011) 424.

Chua, C. W., et al. "Single luminal epithelial progenitors can generate prostate organoids in culture." Nature cell biology 16.10 (2014): 951-961.

Ebert, A. D., et al. "Induced pluripotent stem cells from a spinal muscular atrophy patient" Nature 457.7227 (2009) 277-280.

Howden, S. E., et al. "Genetic correction and analysis of induced pluripotent stem cells from a patient with gyrate atrophy." Proceedings of the National Academy of Sciences 108.16 (2011): 6537-6542.

Knight, G. T., et al. "Micropatterned, clickable culture substrates enable in situ spatiotemporal control of human PSC-derived neural tissue morphology." Chemical Communications 51.25 (2015): 5238-5241.

Lancaster, M. A. et al. "Organogenesis in a dish: modeling development and disease using organoid technologies." Science 345. 6194 (2014): 1247125.

Lancaster, M. A., et al. "Cerebral organoids model human brain development and microcephaly " Nature 501.7467 (2013): 373.

Lippmann, E. S., et al. "Defined human pluripotent stem cell culture enables highly efficient neuroepithelium derivation without small molecule inhibitors." Stem Cells 32.4 (2014): 1032-1042.

Marti-Figueroa, C. R., et al. "The case for applying tissue engineering methodologies to instruct human organoid morphogenesis." Acta biomaterialia 54 (2017): 35-44.

McNulty, J. D., et al. "Micro-injection molded, poly (vinyl alcohol)-calcium salt templates for precise customization of 3D hydrogel internal architecture." Acta biomaterialia 95 (2019): 258-268.

Spence, J. R., et al. "Directed differentiation of human pluripotent stem cells into intestinal tissue in vitro." Nature 470.7332 (2011): 105-109.

Stewart, R., et al. "Comparative RNA-seq analysis in the unsequenced axolotl: the oncogene burst highlights early gene expression in the blastema." PLoS computational biology 9.3 (2013). E1002936.

Takebe, T., et al. "Vascularized and functional human liver from an iPSC-derived organ bud transplant." Nature 499.7459 (2013): 481-484.

Thomson, J. A., et al. "Embryonic stem cell lines derived from human blastocysts." science 282.5391 (1998) 1145-1147.

Xia, Y., et al. "Directed differentiation of human pluripotent cells to ureteric bud kidney progenitor-like cells." Nature cell biology 15.12 (2013): 1507-1515.

Yu, J., et al. "Human induced pluripotent stem cells free of vector and transgene sequences." Science 324.5928 (2009): 797-801.

Yu, J., et al. "Induced pluripotent stem cell lines derived from human somatic cells." science 318.5858 (2007) 1917-1920.

\* cited by examiner

FIGS. 5A-5E, CONTINUED
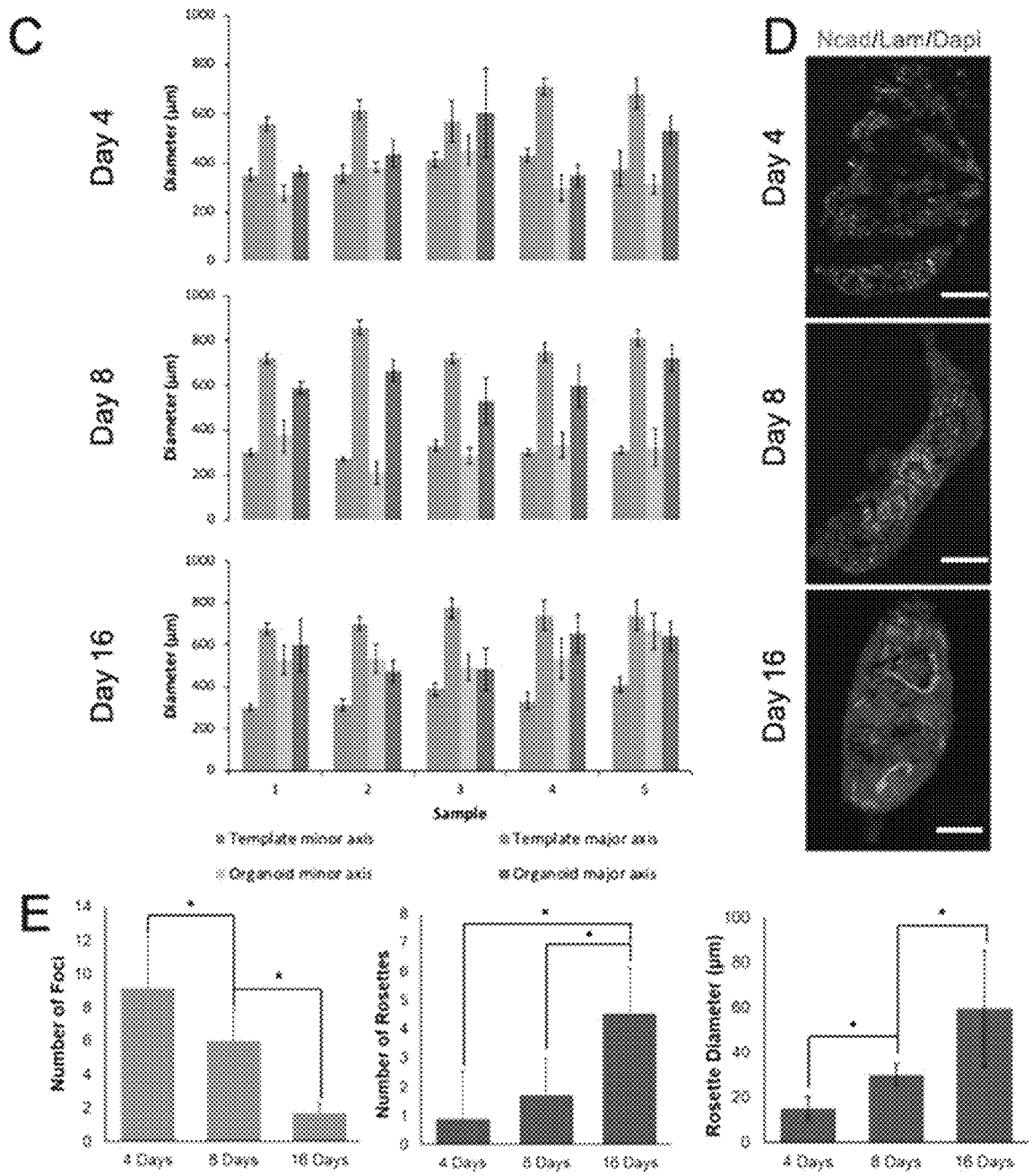

METHODS FOR CONTROLLED INDUCTION OF 3D CYLINDRICAL NEUROEPITHELIAL TUBES

CROSS-REFERENCE TO RELATED APPLICATIONS

This application claims the benefit of U.S. Provisional Application No. 62/746,373, filed on Oct. 16, 2018, which is incorporated by reference herein in its entirety for all purposes.

STATEMENT REGARDING FEDERALLY SPONSORED RESEARCH OR DEVELOPMENT

This invention was made with government support under 1651645 awarded by the National Science Foundation. The government has certain rights in the invention.

BACKGROUND

Human pluripotent stem cells (hPSCs), including human embryonic stem cells (hESCs) and induced pluripotent stem cells (hiPSCs), provide unlimited potential for engineering a wide variety of in vitro tissue models to investigate human physiology and disease. Human pluripotent stem cells (hPSCs) in two dimensional (2D) and three dimensional (3D) aggregate cultures possess the ability to spontaneously differentiate and self-organize, a.k.a. morph, into tissues, a.k.a. organoids, resembling the microscale structure and functions of primordial organs such as the brain, eye, kidney, and gut. These organoids provide unprecedented biomimicry for studying development and disease in vitro and within a human genetic context. However, while spontaneous morphogenesis enables organoid derivation, this same property results in highly non-standardized tissue products.

The current gold standard of central nervous system (CNS) organoid generation involves long-term 3D bioreactor culture of hPSC-derived neural stem cell (NSC) aggregates. The NSCs spontaneously morph into organoids containing unprecedented microscale formations of primordial CNS structures, e.g. cortical, retinal, and cerebellar tissues. However, the organoid's macroscale anatomy, which includes macroscale morphology, cytoarchitecture (i.e., the spatial organization of different cell and tissue phenotypes), and cellular composition, are inconsistent and non-mimetic of the highly-stereotyped CNS. This is due to the in vitro absence of spatial and temporal cues that robustly instruct micro-thru-macroscale CNS morphogenesis in vivo, including physical limitations on tissue morphology and morphogen gradients that spatially pattern diverse cell and tissue phenotypes. Thus, the morphogenesis that occurs within these organoid cultures is uncontrolled, spontaneous and highly variable, leading to an inability to generate standardized protocols. For example, at the onset of organoid derivation, uncontrolled NSC morphogenesis results in random formation of numerous neural tube-like structures, a.k.a. neural rosettes, in contrast to the singular neural tube that forms the primordial anlage and organizational center of CNS morphogenesis in vivo. This results in CNS organoids containing multiple morphogenesis centers, which inevitably confounds their in vitro development and impedes macroscale biomimicry. Such shortcomings of current culture methodologies to robustly instructed controlled in vitro morphogenesis of CNS organoids limits the scalability and clinical translatability of this powerful experimental platform.

Thus, there is an ongoing need for improved methods and compositions for in vitro directed differentiation of human pluripotent stem cells, neuromesodermal progenitors, and neural stem cells into 3D engineered neuroepithelial tubes and other engineered organoids.

BRIEF SUMMARY

Described herein are methods, compositions, and kits for making engineered biomimetic 3D organoid structures in vitro and biomimetic 3D neuroepithelial tube structures.

In a first aspect, provided herein is a method of preparing an engineered biomimetic 3D organoid in vitro. The method can comprise or consist essentially of the steps of (a) providing a hydrogel having a channel therein, the channel having a first end and a second end; (b) sealing one or more of the first and second ends of the channel; (c) seeding the channel opposite one of the sealed ends of the hydrogel with human pluripotent stem cells (hPSCs), (d) contacting the hydrogel comprising the hPSC-seeded channel to an alginate solution, and then contacting the alginate-contacted hydrogel to a divalent cation solution, thereby producing a hPSC-seeded channel encapsulated in cross-linked hydrogel, and (e) culturing the encapsulated hPSC-seeded channel in a culture medium for about four (4) to about sixteen (16) days for the hPSCs within the channel to differentiate into neuroepithelial cells, whereby a biomimetic 3D organoid comprising polarized neuroepithelial cells and having microscale cellular organization similar to that of an in vivo developing human neural tube is obtained.

The hydrogel can be an alginate hydrogel. The divalent cation solution can be a calcium chloride ($CaCl_2$) solution. In some cases, sealing comprises contacting the first end or the second end of the channel to an alginate solution and contacting the alginate-contacted end to a divalent cation solution, thereby producing a channel comprising a sealed end and an unsealed end. In such cases, seeding the channel can comprise injecting a hPSC suspension having a cell density of about 500,000 cells/μl or less into the unsealed end. In other cases, sealing comprises contacting the first end and the second end of the channel to an alginate solution and contacting each alginate-contacted end to a divalent cation solution, thereby producing a channel comprising a first sealed end and a second sealed end. In such cases, seeding the channel can comprise injecting a hPSC suspension having a cell density of about 500,000 cells/μl or less into the first sealed end or the second sealed end. The method can further comprise re-sealing the end into which the hPSC suspension is injected, where re-sealing comprises; contacting an alginate solution to the hPSC suspension-injected end; and contacting the alginate-contacted end to a divalent cation solution to cross-link the alginate, thereby producing a hPSC-seeded channel comprising a sealed end and a re-sealed end.

The biomimetic 3D organoid can be a biomimetic neuroepithelial organoid comprising polarized neural stem cells. The channel can be substantially tubular. The diameter of the substantially tubular channel can be between about 50 μm to about 700 μm. The diameter of the substantially tubular channel can be between about 100 μm to about 300 μm. The culture medium can be sufficient to promote the self-organization and spontaneous morphogenesis of the hPSCs into neuroepithelial organoids. The culture medium can be a neural differentiation medium comprising water, salts, amino acids, vitamins, a carbon source, a buffering agent, selenium, ascorbate, insulin, transferrin, and a Rho kinase (ROCK) inhibitor. The hydrogel comprising the cell-seeded channel can be cultured within a spinner flask containing the neural differentiation medium. The hydrogel can be produced by a method comprising or consisting essentially of the steps of (a) providing a sacrificial template of a predefined shape immobilized within a casting chamber, (b) introducing into the casting chamber a volume of hydrogel polymer solution sufficient to surround the sacrificial template, (c) contacting the hydrogel polymer with a crosslinking solution to form a hydrogel shell surrounding the sacrificial template, and (d) removing the sacrificial template thereby providing a hydrogel with a channel therein. The sacrificial template can be a water soluble thermoplastic-divalent cationic salt composite material. The sacrificial template can be a poly(vinyl alcohol) material coated in divalent cations.

In another aspect, provided herein is an engineered in vitro biomimetic 3D neuroepithelial organoid structure, where the engineered in vitro biomimetic 3D neuroepithelial organoid structure is made by a method provided herein.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention and to cover all modifications, equivalents and alternatives. Reference should therefore be made to the claims recited herein for interpreting the scope of the invention.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein.

Figure 1:
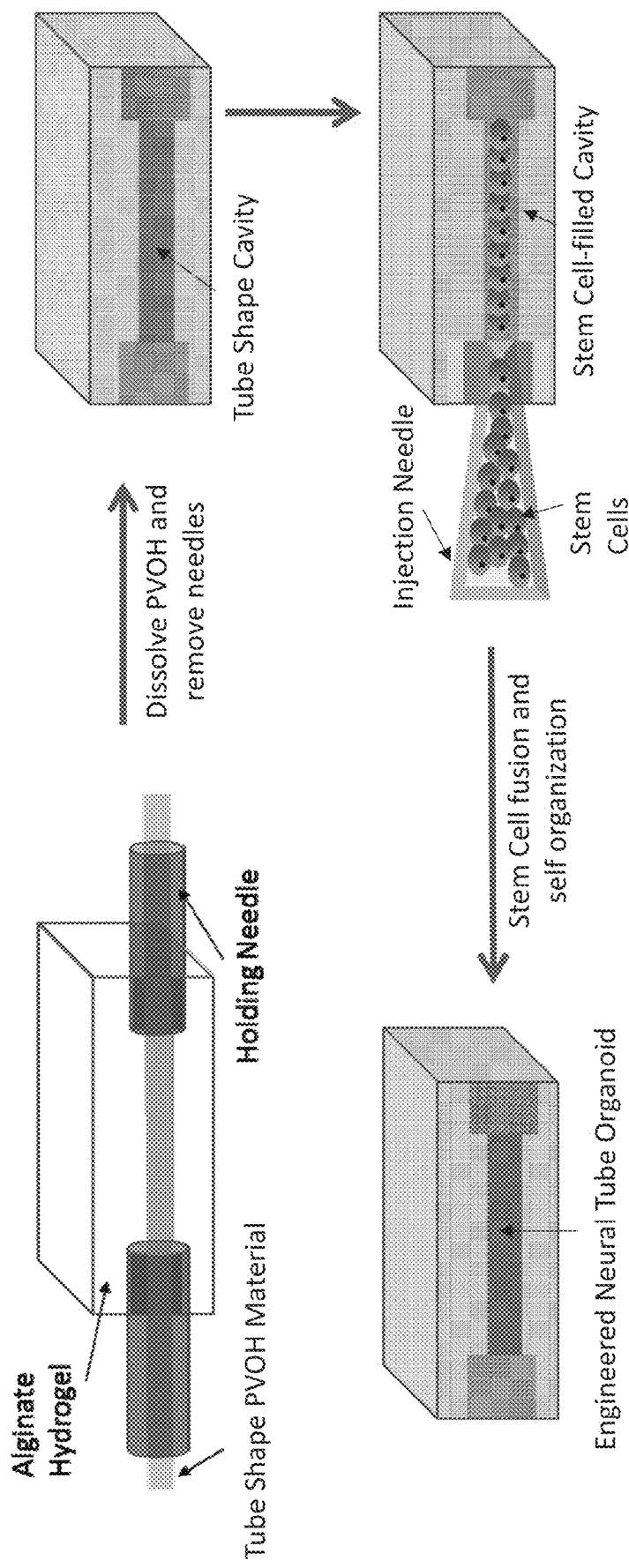
FIG. 1 depicts a method of making hydrogels with tube like shapes into which stem cells are injected and then organize to form a neuroepithelial tube organoid.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

The present invention relates at least in part to the inventors' unexpected discovery of methods to produce an engineered three-dimensional (3D) culture system for in vitro generation of an engineered human neuroepithelial tube. By directing differentiation of stem cells in a hollow tube, the inventors developed in vitro organoids that mimic the in vivo neural tube structure and morphology using defined conditions. The methods described herein for regulating the microscale morphology of 3D tubal neuroepithelial organoids derived from hPSCs, which replicates the primordial neural tube in vivo, may be adaptable to other morphologies and tissues, especially tissues which form tubular structures during development (e.g., developing heart tube, digestive tract, etc.).

In the central nervous system (CNS), the brain and spinal cord develop from a hollow tube of polarized neuroepithelial cells (NECs), a.k.a. neural stem cells, called the neuroepithelial tube. In vitro, NECs spontaneously polarize during differentiation to form similar neuroepithelial tube analogs, i.e. neural rosette structures, in both two-dimensional (2D) and 3D culture.

As described in the Examples below, the present disclosure provides reproducible engineering of 3D neuroepithelial tubes made by a method using cylindrical sacrificial materials such as, for example poly(vinyl) alcohol (described in U.S. patent application Ser. No. 14/961,033, incorporated by reference in its entirety) or fishing line to form channels through alginate hydrogels. The sacrificial material is used to cast internal channels inside of alginate hydrogels (FIG. 1), which are then injected with hPSCs at an optimal cell density. The hPSCs differentiate in situ using a chemically defined medium and spontaneously organize into a polarized tube of neural stem cells (e.g., neuroepithelial cells (NECs)) expressing N-Cadherin at tube's apical surface and secreting a laminin-rich basement membrane at the tube's basal surface (see, for example, left image of FIG. 7B). These neuroepithelial tube organoids approximate the morphology of the germinal neural tube in the developing human embryo. The present invention provides methods for reproducible morphogenesis of 3D neuroepithelial organoids that yield a more biomimetic and, therefore, more physiologically relevant 3D tissue model. Similar epithelial tube formation characterizes the developmental process of other human organs as well, e.g., the heart and digestive system. Thus, analogous methods could be applied to standardize biomimetic morphogenesis of organoids from these tissues/organ systems.

The presently described methods allow for unprecedented control of neural tissue morphogenesis to form 3D organoid structures, which the current state-of-art methods lack. This discovery represents a significant advancement and universal basis for engineering anatomically biomimetic human CNS organoids in vitro. The inventors' discovery also provides an important opportunity to model patterning of the human CNS in an in vitro 3D model, to study neural development and disease in a biomimetic in vitro human model, and to identify materials and combinatorial strategies for in vitro tissue engineering.

I. Definitions

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, the following terminology will be used in accordance with the definitions set out below.

As used herein, the term "pluripotent stem cell" (hPSC) means a cell capable of continued self-renewal and of capable, under appropriate conditions, of differentiating into cells of all three germ layers. hPSCs exhibit a gene expression profile that includes SOX2$^+$ and OCT4$^+$. Examples of human PSCs (hPSCs) include human embryonic stem cells (hESCs) and human induced pluripotent stem cells (hiPSCs). As used herein, "iPS cells" refer to cells that are substantially genetically identical to their respective differentiated somatic cell of origin and display characteristics similar to higher potency cells, such as ES cells, as described herein. The cells can be obtained by reprogramming non-pluripotent (e.g., multipotent or somatic) cells.

As used herein, "pluripotency" means a cell's ability to differentiate into cells of all three germ layers.

As used herein, "neural stem cell" (NSC) refers to a multipotent stem cell that is PAX6+/Sox2$^+$ and is capable of differentiating into neurons or glia of the CNS or peripheral nervous system (PNS). As used herein, neuroepithelial cells (NECs) refer to neural stem cells that are polarized epithelial cells exhibiting apico-basal polarity within neural rosette structures.

As used herein, the term "neuromesodermal progenitors" (NMPs) refers to human pluripotent stem cell-derived cells having the following gene expression profile: SOX2+/OCT4-/T+/PAX6-. NMPs are also referred to as caudal lateral epiblasts.

As used herein the term "neuroepithelial tube" refers to an engineered 3D organoid structure made by the methods described herein that replicates primordial neural tube in vivo as demonstrated by the polarization of cells within the neuroepithelial tube as detected by expression of laminin and N-cadherin.

As used herein, the term "neural rosette" refers to a neuroepithelial tube analog comprising neuroepithelial cells (NECs) that forms when human pluripotent stem cells are neurally differentiated in two-dimensional (2D) and three-dimensional (3D) culture. Neural rosette morphology can be elucidated by apical N-cadherin localization along constituent cell membranes with apico-basal polarity.

A "biological molecule" or "biomolecule" as used in the context of this invention refers to a molecule that is substantially of biological origin. Such molecules may include non-naturally occurring components that mimic a naturally occurring component, e.g., a non-naturally occurring amino acid.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "cell culture medium" as used herein (also referred to herein as a "culture medium" or "medium" or "culture media") is a medium for culturing cells containing nutrients that maintain cell viability and support proliferation.

The term "chemically defined culture medium" or "chemically defined medium," as used herein, means that the chemical structure and quantity of each medium ingredient is definitively known.

As used herein, "a medium consisting essentially of" means a medium that contains the specified ingredients and those that do not materially affect its basic characteristics.

"Supplemented," as used herein, refers to a composition, e.g., a medium comprising a supplemented component (e.g., retinoic acid, fibroblast growth factor (FGF)). For example a medium "further supplemented" with retinoic acid (RA) or a FGF, refers to the medium comprising RA or FGF, and not to the act of introducing the RA or FGF to the medium.

As used herein, "effective amount" means an amount of an agent sufficient to evoke a specified cellular effect according to the present invention.

As used herein, the terms "xenogen free" and "xeno-free" are used interchangeably and refer to a material that is free of or substantially free of xenogeneic material or undefined components that are derived from a non-human source.

"Neural differentiation base medium," as used herein, refers to a medium capable of promoting and supporting differentiation of human pluripotent stem cells towards a neural lineage, e.g., towards neuroectoderm and neuroepithelium. A neural differentiation base medium can include, but is not limited to E6 medium, as described herein and in U.S. Patent Publication No. 2014/0134732.

The terms "purified" or "enriched" cell populations are used interchangeably herein, and refer to cell populations, ex vivo, that contain a higher proportion of a specified cell type or cells having a specified characteristic than are found in vivo (e.g., in a tissue).

As used herein, "serum-free" means that a medium does not contain serum or serum replacement, or that it contains essentially no serum or serum replacement. For example, an essentially serum-free medium can contain less than about 1%, 0.9%, 0.8%, 0.7%, 0.6%, 0.5%, 0.4%, 0.3%, 0.2% or 0.1% serum, wherein the culturing capacity of the medium is still observed.

As used herein, "substantially free of" means that a culture medium or other composition or solution is free or nearly free of a particular component. For example, "substantially free of putrescine" means no putrescine is added to a cell culture medium above and beyond any putrescine present in the base medium, e.g., DMEM/F12. Alternatively, "substantially free of putrescine" means a final putrescine concentration less than or equal to 0.08 mg/L.

As used herein, "viability" means the state of being viable. Pluripotent cells that are viable attach to the surface and do not stain with the dye propidium iodide absent membrane disruption. Short term viability relates to the first 24 hours after plating the cells in culture. Typically, the cells do not proliferate in that time.

As used herein, the term "sacrificial template" or "sacrificial material" refers to a material that maintains its shape during fabrication of the hydrogel around such sacrificial template or material, but is able to be removed after hydrogel fabrication to provide a cavity or channel in the shape of the sacrificial template or sacrificial material.

As used herein, the term "cross-linking" or "cross-linked" refers to a bond that links one polymer chain to another to form the hydrogel. These links may be covalent bonds or ionic bonds.

The term "cross-linking agent," "hydrogel cross-linking agent," "cross-linker" and "hydrogel cross linker" are used herein interchangeably to refer to an agent (e.g., calcium cations) that initiates cross-linking of hydrogel polymers (e.g., alginate polymers) into a hydrogel. A suitable hydrogel cross-linking agent is selected based upon the specific type of hydrogel polymer to be cross-linked. For example, for divalent cross-linkable hydrogel polymers such as alginate, divalent cations such as calcium, magnesium, or barium may be used. In other cases, depending on the selected hydrogel polymer, the hydrogel cross-linker may be an anionic agent or a free-radical generator/initiator.

As used herein, the term "about," when referring to a value or to an amount of mass, weight, time, volume, concentration, percentage or a physical dimension such as length, width, or diameter, is meant to encompass variations of in some embodiments+20%, in some embodiments ±10%, in some embodiments+5%, in some embodiments+ 1%, in some embodiments+0.5%, and in some embodiments+0.1% from the specified value or amount, as such variations are appropriate to perform the disclosed methods.

II. Methods, Compositions, and Organoids

Methods and systems for making an engineered biomimetic 3D organoid in vitro are provided herein. The methods provide the ability to reproducibly engineer tubular 3D organoids, including but not limited to engineered neuroepithelial tubes comprising neuroepithelial cells, using a hydrogel scaffold. The method is depicted, for example, in FIGS. 1, 2, and 3. As used herein, the terms "synthetic" and "engineered" are used interchangeably and refer to a non-naturally occurring tissue material that has been created or modified by the hand of man (e.g., formed in vitro using man-made materials) or is derived using such material (e.g., a device comprising the engineered material). As used herein, the term "organoid" refers to a tissue-like structure (i.e., exhibiting structural properties of a particular tissue type) that resembles a developing organ and is assembled in vitro by the separate addition and self-organization of cell types including, but not limited to, pluripotent stem cells or neural stem cells. See, e.g., Lancaster and Knoblich, *Science* 345(6194) (2014). In exemplary embodiments of the invention, an engineered organoid comprises a three-dimensional structure and provides a physiologically relevant microenvironment for analysis or perturbation of cell-cell interactions, cell-matrix interactions, and morphogenesis in three-dimensional culture. In some cases, an organoid culture system provides a microenvironment that at least partially recapitulates human neuroepithelial tube development.

The method comprises (a) providing a hydrogel having a channel therein, the channel having a first end and a second end, (b) sealing one or more of the first and second ends of the channel, (c) seeding the channel opposite a sealed end of the channel with a sufficient amount of human pluripotent stem cells (hPSCs), (d) sealing one or more of the first end and second end of the channel, and (e) culturing the hydrogel comprising the cell-seeded channel in a culture medium for a sufficient amount of time for the hPSCs within the channel to differentiate into a biomimetic 3D organoid. The resultant biomimetic 3D organoid can have nanoscale or microscale cellular organization similar to that of the corresponding in vivo developing organ. As used herein the term "microscale cellular organization" means that structural organization of cellular components (also known as "cytoarchitecture") of a biomimetic 3D organoid is similar to a corresponding in vivo tissue at the microscale level, meaning on the order of sizes of less than 1000 μm, and more preferably less than 100 μm. In some cases, the cellular organization of the biomimetic 3D organoid is similar to a corresponding in vivo tissue at a nanoscale level, meaning on the order of sizes less than 10 am, and more preferably on the order of 100 nm or smaller.

As depicted in FIG. 1, in one example, the present methods use a hydrogel to form a structured hydrogel having a channel therein in which to form the 3D organoid within. The channel within the hydrogel has a first end and a second end. It is within the channel that hPSCs are seeded and can differentiate into 3D organoids. In preferred embodiments, one end of the channel are sealed prior to seeding cells within the channel. Preferably, seeding comprises injecting a cell solution through an un-sealed hydrogel end opposite of a hydrogel-sealed end, whereby cells of the cell solution are densely packed into the channel and the aqueous portion of the cell solution diffuses through the hydrogel and/or hydrogel-sealed end. Methods of forming a channel include, but are not limited to, the methods as described in U.S. Patent Publication No. 20170157802. For example, a cylindrical sacrificial material can be used to form channels through alginate hydrogels.

In some embodiments, the hydrogel is prepared using a polymer solution. The polymer solution can comprise a divalent cation-crosslinkable polymer selected from the group consisting of alginate, polysaccharides, xanthan gums, natural gum, agar, agarose, carrageenan, fucoidan, furcellaran, laminaran, hypnea, eucheuma, gum arabic, gum ghatti, gum karaya, gum tragacanth, locust beam gum, arabinogalactan, pectin, amylopectin, and ribo- or deoxyribonucleic acids. In some preferred embodiments, the hydrogel polymer solution comprises alginate.

In some cases, the hydrogel may be produced by three-dimensional printing. As used herein, the term "three-dimensional printing" (also "3D printing") generally refers to a process or method for generating a 3D part (or object). Such process may be used to form a 3D printed hydrogel having one or more channels. 3D-printing provides control over the structure of hydrogel that is absent in molded structures. Any appropriate method for printing a 3D hydrogel having the dimensions and properties described herein can be used. In some cases, 3D printing of a hydrogel comprises driving a laser printing system by a solid-model computer-aided design (CAD) modeling system, where the CAD modeling system comprises a computer that controls the laser printing system based on model designed beforehand using computer aided design (CAD). Preferably, the predefined CAD model is configured to print a hydrogel comprising one or more channels. In one example, CAD model is configured for 3D printing of a hydrogel comprising a tubular channel or a channel having another suitable shape (e.g., oval, square). In some cases, the channel has a diameter from about 50 µm to about 700 µm, preferably from about 100 µm to about 300 µm. For example, suitable diameters of the channel include, but are not limited to, e.g., about 100 µm, about 150 µm, about 200 µm, about 225 µm, about 250 µm, about 275 µm, about 300 µm, among others. In a preferred embodiment, the diameter is about 100 µm to about 300 µm.

In some cases, the hydrogel may be made by (a) providing a sacrificial template of a predefined shape immobilized within a casting chamber, and (b) introducing into the casting chamber a volume of hydrogel polymer solution sufficient to surround the sacrificial template, (c) contacting the hydrogel polymer solution with a crosslinking solution in a sufficient amount to crosslinked the hydrogel polymer in the solution to form a hydrogel shell surrounding the sacrificial template, and (c) removing the sacrificial template, thereby providing a hydrogel with a channel therein. In one example, the predefined shape is cylindrical. In such cases, the channel adopts a tube shape, however other suitable cross-sectional shapes (e.g., oval, square) are contemplated. In some cases, the channel formed through the hydrogel (e.g., alginate hydrogel) has a circular shape in cross-section with a diameter from about 50 µm to about 700 µm, preferably from about 100 µm to about 300 µm. For example, suitable diameters of the channel include, but are not limited to, e.g., about 100 µm, about 150 µm, about 200 µm, about 225 µm, about 250 µm, about 275 µm, about 300 µm, among others. In a preferred embodiment, the diameter is about 100 µm to about 300 µm.

In some cases, the crosslinking solution is a solution comprising gelling agents including but not limited to metallic ions, such as $Pb^{2+}$, $Ba^{2+}$, $Fe^{3+}$, $Al^{3+}$, $Cu^{2+}$, $Cd^{2+}$, $Ho^{3+}$, $Ca^{2+}$, $Zn^{2+}$, $Co^{2+}$, $Ni^{2+}$, $Mn^{2+}$, and $Mg^{2+}$. For example, the crosslinking solution is a divalent cation solution comprising cations selected from calcium, barium, strontium, copper, zinc, magnesium, manganese, cobalt, lead, iron, nickel, chromium, and aluminum ions. In some cases, divalent cation solution is a calcium chloride solution.

Suitable temperatures for crosslinking the hydrogel are known in the art, and include, but are not limited to, for example, about 4° C. to about 45° C., for example, about 37° C.

Any suitable material can be used as a sacrificial template to form channels in a hydrogel. In some cases, the sacrificial template comprises a water-soluble thermoplastic-divalent cation composition material. In other cases, the annular sacrificial template material is fishing line (e.g., monofilament fishing line) which is commercially available in various diameters (thicknesses). For example, the fishing line may by nylon fishing line having a diameter of about 100 µM to about 300 µm, for example, 250 µm.

In some cases, it will be advantageous to produce a sacrificial template by three-dimensional printing. As used herein, the term "three-dimensional printing" (also "3D printing") generally refers to a process or method for generating a 3D part (or object). Such process may be used to form a 3D part (or object), such as a 3D sacrificial template material to form channels in a hydrogel. Any appropriate method for printing a three-dimensional sacrificial template having the dimensions and properties described herein can be used. In some cases, 3D printing of a sacrificial template comprises driving a laser printing system by a solid-model computer-aided design (CAD) modeling system, where the CAD modeling system comprises a computer that controls the laser printing system based on a CAD model of the desired material and additional parameters.

In some embodiments, the sacrificial template comprises or is coated with divalent cations whereby the divalent cations, when in contact with the hydrogel polymer, diffuse from the sacrificial template and crosslink the hydrogel polymer in the solution to form a hydrogel shell surrounding the sacrificial template. For example, the sacrificial template can be fishing line coated with divalent cations. In such cases, any appropriate method of coating the fishing line can be used including, without limitation, by dipping the fishing line in a divalent cation solution (e.g., $CaCl_2$ solution).

Suitable water-soluble thermoplastic-divalent cation composite materials are known in the art, and include, but are not limited to, for example, poly(vinyl alcohol), poly(ethyleneoxide), poly(ethylene glycol), poly(lactic acid), poly(glycolic acid), and combinations thereof. In some examples, the water-soluble thermoplastic is poly(vinyl alcohol). In some embodiments, the water-soluble thermoplastic-divalent cationic salt composite material is a poly(vinyl alcohol)-divalent cation composite material, and the amount of the divalent cationic salt is insufficient to cause excessive crosslinking of the poly(vinyl alcohol).

In some embodiments, the poly(vinyl alcohol)-divalent cationic composite material comprises a divalent cationic salt having a solubility of at least 0.01 g/ml to about 10 g/ml in water at 30° C. In some embodiments, the poly(vinyl alcohol)-divalent composite cationic material comprises a calcium salt selected from the group consisting of: calcium acetate, calcium selenate, and calcium formate. In some embodiments, the poly(vinyl alcohol)-divalent cationic composite material comprises calcium acetate. In some embodiments, where the calcium salt used is calcium acetate, the poly(vinyl alcohol)-divalent cationic composite material comprises about 5% to about 30% (w/w) calcium acetate. In some embodiments, the poly(vinyl alcohol)-divalent cationic composite material comprises about 10% calcium acetate. I In some embodiments, the divalent cationic salt is a calcium salt, a magnesium salt, or a barium salt. In some embodiments the sacrificial template comprises a calcium salt. In some embodiments the poly(vinyl alcohol)-divalent cationic salt composite material is a poly(vinyl alcohol)-calcium salt composite material. In some embodiments, where the poly(vinyl alcohol)-divalent cation composite material comprises a calcium salt, the calcium salt is calcium acetate.

Methods of forming the sacrificial template and removing the sacrificial template from the hydrogel are described in U.S. Patent Publication No. 20170157802. For example, the sacrificial template may be dissolved by incubation at a suitable temperature in an aqueous solutions (e.g., water or cell culture medium). Suitable temperatures for dissolving are known in the art and include, but are not limited to, for example, temperate to warm (e.g., about 20° C. to about 40° C.). In another example, when nylon fishing line is used, the fishing line is physically removed from the hydrogel by pulling at one end of the fishing line until it is removed from the hydrogel.

Figure 2:
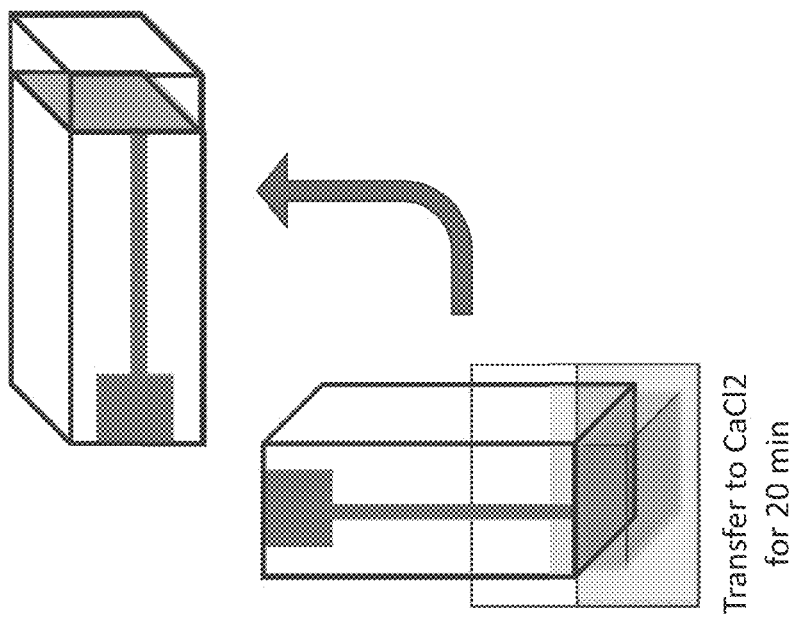
FIG. 2 depicts an exemplary method of making a hydrogel with one closed end for injection of the cells to make a neuroepithelial tube.
Figure 2:
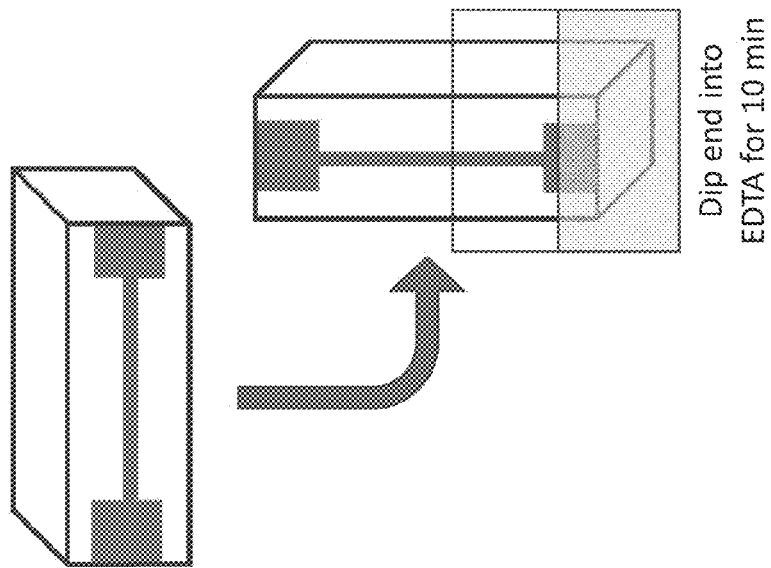

One of the channel, once formed, may be closed or sealed as depicted in FIG. 2 prior to seeding thechannel with cells. Suitable methods of sealing or closing one end, include, for example, coating the end of the hydrogel with additional hydrogel, e.g., alginate hydrogel. FIG. 2 illustrates coating an end of the hydrogel with a layer of alginate hydrogel. The alginate layer is of sufficient thickness as to allow medium to flow out from the channel but to retain the seeded cells within the channel. Suitable thicknesses of the alginate hydrogel layer can range from about 50 µm to about 500 µm in thickness (e.g., about 50 µm, 60 µm, 70 µm, 80 µm, 90 µm, 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, 500 µm inclusive), preferably about 250 µm to about 500 µm thick.

Suitably, the method comprises seeding the hPSCs into the channel of the hydrogel at a sufficient concentration to form a single contiguous cell aggregate throughout the channel within 6 to 24 hours of culture. Seeding of the cells is preferably performed after one end of the channel is closed or sealed, allowing for the ability to densely pack the channel with seeds. In some cases, however, seeding can comprise injecting a cell solution through a hydrogel-sealed end, whereby cells of the cell solution are densely packed into the channel and the aqueous portion of the cell solution diffuses through the hydrogel. In some cases, the sealed end through which the cell solution is injected can be re-sealed using another layer of hydrogel (e.g., alginate hydrogel). It will be understood that seeding parameters should be selected to minimize shear strain when manipulating the cells in solution, to avoid excessive cell death, and to provide a density of cells along the entire length of the channel sufficient to result in formation of a single contiguous cell aggregate throughout within 6 to 24 hours of culture post-injection.

The cell concentration within the injection solution plays an important role in satisfactory seeding of the channel. As FIG. 4 depicts, experiments were performed to determine the optimal concentration for cell suspension injections into the hydrogels. If the concentration is too low, there is a risk not having enough cells to form a single contiguous tissue inside the hydrogel. For example, if the seeded cells are sparse, they form small, multiple aggregates within the hydrogel. If the density is too high, there is a risk of inducing high shear on the cells causing altered cell behavior and potentially cell death. Suitable cell suspension concentrations for injection of cells into the channel are cell suspension concentrations of up to 500,000 ($5\times10^5$) cells/µl, for example, from about 50,000 cells/µl to about 500,000 cells/µl, preferably about 100,000 cells/µl to about 300,000 cells/µl, more preferably about 150,000 cells/µl to about 300,000 cells/µl, preferably about 200,000 cells/µl to about 300,000 cells/µl, for example, 250, 000 cells/µl.

Seeding may be done by injection of the cells through a needle into the channel. The size of the injection needle is a size in which shear against the cells when exiting the needle is minimized. The term "needle" used herein refer to needles, pipette tips or other materials that are used to manipulate the cells in solution. Suitable needle sizes (e.g., needle diameters) range from about 100 µm to about 400 µm (e.g., 100 µm, 125 µm, 150 µm, 175 µm, 200 µm, 225 µm, 250 µm, 275 µm, 300 µm, 325 µm, 350 µm, 375 µm, 400 µm, inclusive), preferably from about 250 µm to about 300 µm, alternatively about 280 µm to about 300 µm.

Any suitable progenitor cells can be used to seed the channel which can form an organoid structure. For example, pluripotent stem cells (PSCs), including embryonic stem cells (ESCs) and induced pluripotent stem cells (iPSCs) can be used. For making engineered neuroepithelial neural tubes, any suitable progenitor cells that is able to form the polarized cellular structure found in the engineered neuroepithelial tube (e.g., polarized staining of laminin and N-cadherin) can be used, including, but not limited to, hPSCs, neural stem cells (NSCs), or neuromesodermal progenitors (NMPs), among others. For example, other progenitor cells that result in different neural cell fates are contemplated for use in the described methods to make engineered neuroepithelial having forebrain, midbrain, hindbrain, or spinal cord identity. For example, neuromesodermal progenitors (NMPs) may be used to seed a channel to form an engineered neurepithelial tube containing hindbrain and spinal progenitor cells.

In some cases, neural stem cells for use in the methods provided herein are obtained by directed differentiation of human pluripotent stem cells (hPSCs). As used herein, "pluripotent stem cells" appropriate for use according to a method of the invention are cells having the capacity to differentiate into cells of all three germ layers. Suitable pluripotent cells for use herein include human embryonic stem cells (hESCs) and human iPSCs. As used herein, "embryonic stem cells" or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60 andTRA-1-81, and appear as compact colonies having a high nucleus to cytoplasm ratio and prominent nucleolus. ESCs are commercially available from sources such as WiCell Research Institute (Madison, Wis.). As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007).

Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60 or Tra-1-81, but not SSEA-1). Induced pluripotent stem cells, however, are not immediately derived from embryos. As used herein, "not immediately derived from embryos" means that the starting cell type for producing iPS cells is a non-pluripotent cell, such as a multipotent cell or terminally differentiated cell, such as somatic cells obtained from a post-natal individual.

Human iPS cells can be used according to a method described herein to obtain primitive macrophages and microglial cells having the genetic complement of a particular human subject. For example, it may be advantageous to obtain 3D neuroepithelial organoids that exhibit one or more specific phenotypes associated with or resulting from a particular disease or disorder of the particular mammalian subject. In such cases, iPS cells are obtained by reprogramming a somatic cell of a particular human subject according to methods known in the art. See, for example, Yu et al., *Science* 324(5928):797-801 (2009); Chen et al., *Nat. Methods* 8(5):424-9 (2011); Ebert et al., *Nature* 457(7227):277-80 (2009); Howden et al., *Proc. Natl. Acad. Sci. U.S.A* 108(16):6537-42 (2011).

Prior to seeding within the hydrogel, hPSCs (e.g., hESCs or hiPSCs), can be cultured in the absence of a feeder layer (e.g., a fibroblast layer) on a substrate suitable for proliferation of hPSCs, e.g., MATRIGEL™, vitronectin, a vitronectin fragment, or a vitronectin peptide, or Synthemax®. In some cases, the hPSCs are passaged at least 1 time to at least about 5 times in the absence of a feeder layer. Suitable culture media for passaging and maintenance of hPSCs include, but are not limited to, mTeSR® and E8™ media. In some embodiments, the hPSCs are maintained and passaged under xeno-free conditions, where the cell culture medium is a defined medium such as E8 or mTeSR, but the cells are maintained on a completely defined, xeno-free substrate such as vitronectin or Synthemax® (or another type-of self-coating substrate). In one embodiment, the hPSCs are maintained and passaged in E8 medium on vitronectin, a vitronectin fragment, or a vitronectin peptide or a self-coating substrate such as Synthemax®.

In some cases, a second end of the channel is sealed first, and then cells in an injection solution are injected. In such cases, the injection solution is pushed through the sealed end's hydrogel, but the cells are retained within the channel. This allows for the cells to be packed into the channel at a high density.

Figure 3:
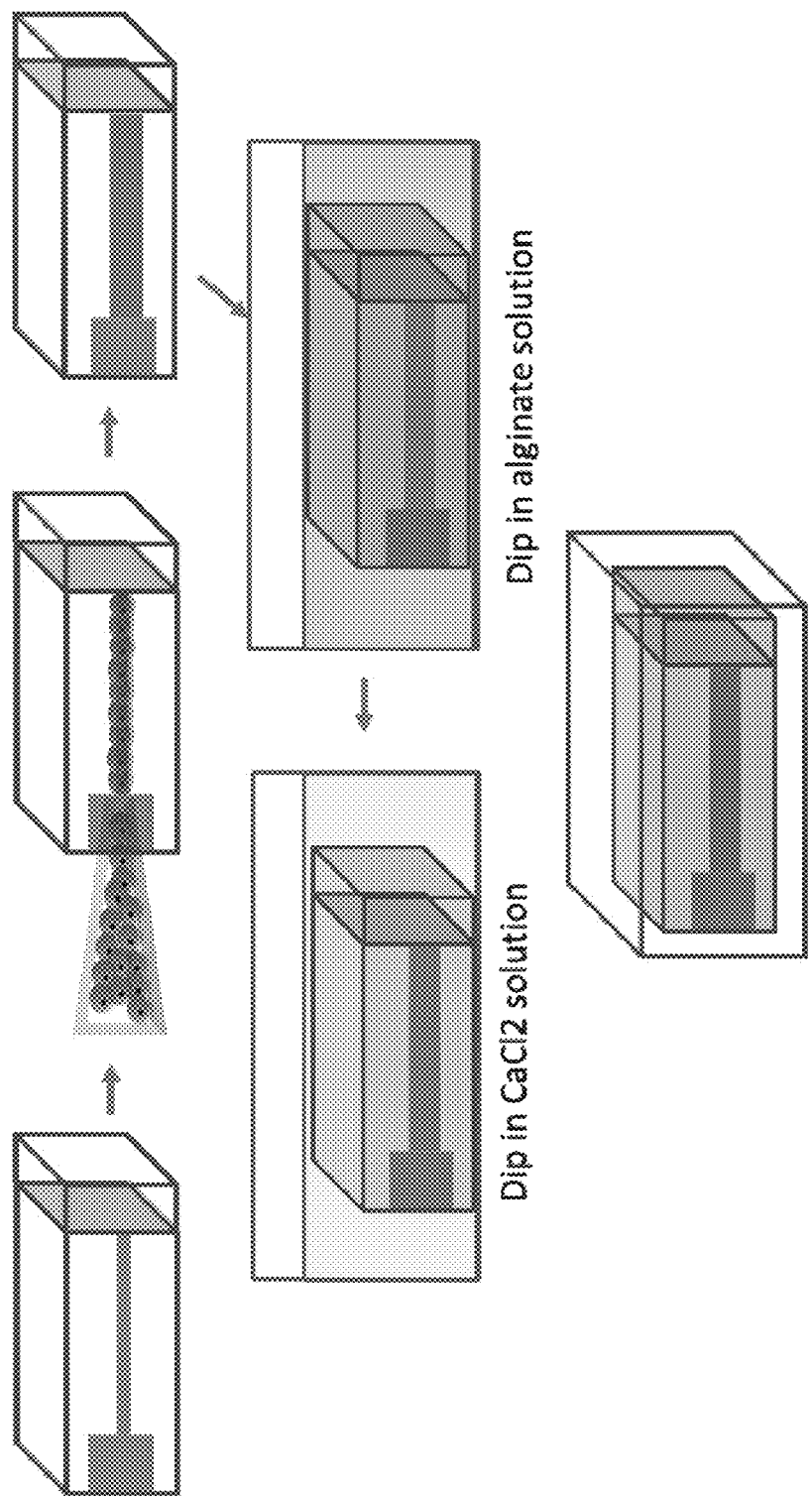
FIG. 3 is an exemplary method for use in closing or sealing the hydrogel containing a neuroepithelial tube.

Once cells are seeded within the channel, is the hydrogel comprising the cell-seeded channel is further encapsulated in hydrogel as depicted in FIG. 3. Encapsulation puts a thicker seal on each end to avoid the cells being pulled out of the hydrogel when culturing in a spinner flask. If one end remains unsealed, the differential pressure created at this end of the channel pulls the cells out of the channel losing all morphological control. In one suitable method, the cell-seeded hydrogel is first dipped in an alginate solution and subsequently dipped in a cation solution (e.g., $CaCl_2$ solution), which allows for a layer of alginate to form around the cell-seeded hydrogel. A sufficient layer of hydrogel is formed around the cell-seeded hydrogel that allows for media transfer to the interior of the channel but retains the cells within the hydrogel channel. Suitable thicknesses of the hydrogel layer are thicknesses sufficient to encapsulate the entire hydrogel, and include, but are not limited to, for example, about 50 μm to about 1 mm or about 500 μm to 1 mm. Other suitable methods of providing a layer of hydrogel are contemplated to be able to be used in the method without departing from the invention. This sealing or encapsulation of the cell-seeded hydrogel allows for the cell-seeded hydrogel to be cultured under conditions used for organoid culture, e.g., spinner flask culture methods.

The hPSCs once seeded may be cultured in differentiation media suitable to differentiate the cells into the organoid. Suitable culture medium conditions are known in the art for differentiating of hPSCs or other progenitor cells into organoid tissue in vitro.

Figures 7A, 7B:
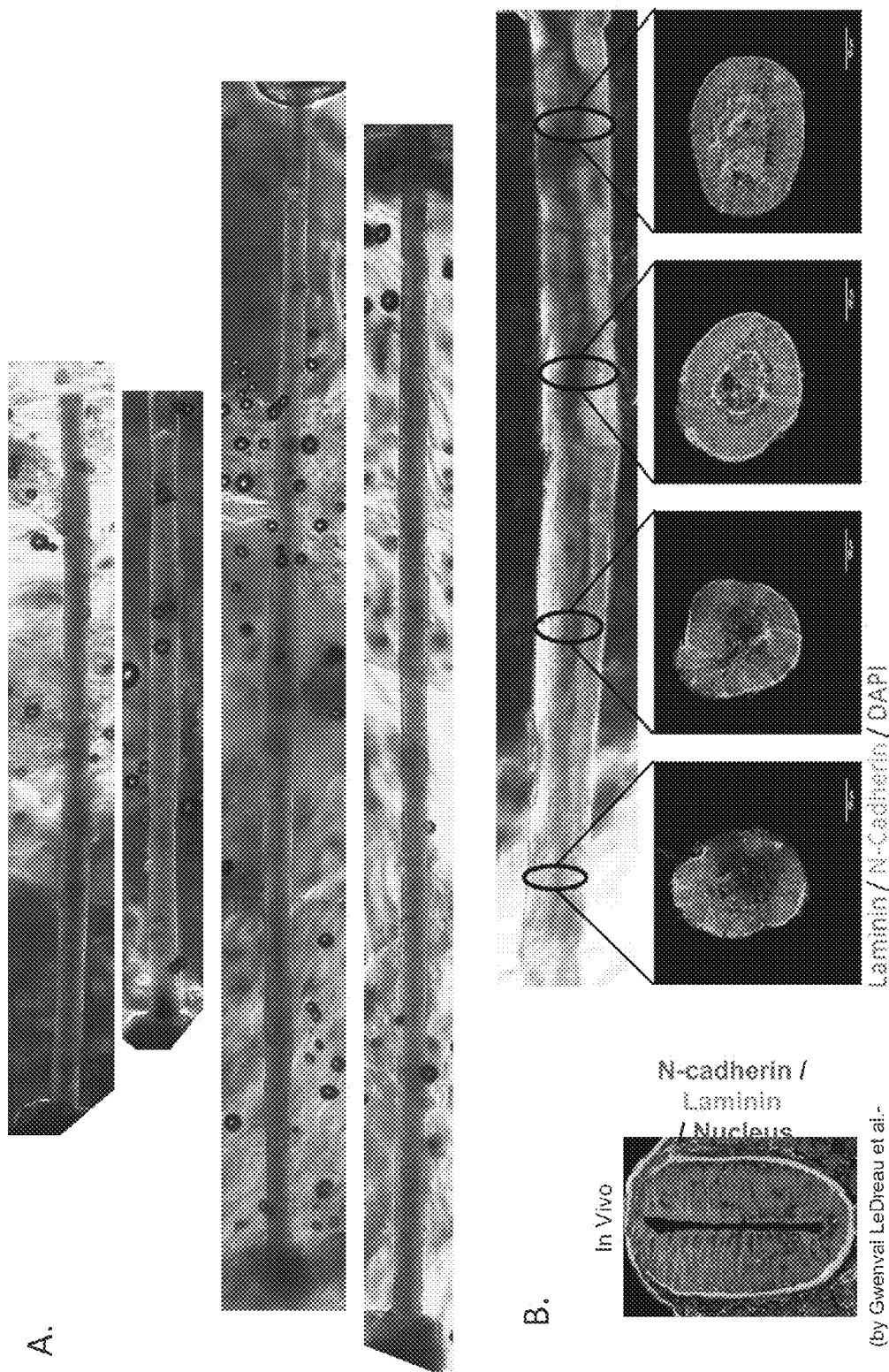
FIGS. 7A-7B present exemplary comparisons of the in vitro engineered neuroepithelial tube and in vivo staining. (A) Exemplary in vitro derived biomimetic neuroepithelial organoids made using methods provided herein. (B) Images shown are cross-sections of engineered neuroepithelial tubes, stained for expression of laminin and N-cadherin. Nuclei were stained with DAPI (blue).

For example, for formation of engineered neuroepithelial tubes, the seeded hPSCs are differentiated within the channel using a chemically defined medium, and organized into a polarized tube of neural stem cells (e.g., neuroepithelial cells (NECs)) expressing N-Cadherin and laminin (see, for example, left image of FIG. 7B). The engineered neuroepithelial tube organoids approximate the morphology of the germinal neural tube in the developing human embryo. The method provides reproducible morphogenesis of 3D neuroepithelial organoids that yields a more biomimetic and, therefore, more physiologically relevant 3D tissue model.

In one example, the culture medium is sufficient to promote the self-organization and spontaneous morphogenesis of the hPSCs into engineered neuroepithelial tube organoids in vitro. Suitable media include, for example, a neural differentiation medium. The cell-seeded hydrogels are cultured for at least 4, 6, 8, or 16 days in suitable culture conditions. Preferably, the cell-seeded hydrogels are cultured for a sufficient time to form the 3D organoid structure, for example, at least 4 days, at least 6 days, at least 8 days, or at least 16 days in culture. In some cases, culture conditions comprise placing a cell-seeded hydrogel in suitable culture medium and culturing in a tissue culture spinner flask. Spinner flasks allow for the exchange of spent medium internally from the hydrogel with fresh medium containing the proper culture conditions to differentiate the hPSCs into the 3D organoid cells.

In various embodiments, the differentiation of hPSCs into neural stem cells is affected by culturing the pluripotent stem cells (PSCs) in any of a number of serum-free media that support differentiation of human pluripotent stem cells into neural stem cells, collectively referred to herein as ("neural differentiation media"). "Neural differentiation medium," as used herein, refers to a medium capable of promoting and supporting differentiation of human pluripotent stem cells towards a neural lineage, e.g., towards neuroectoderm and neuroepithelium. A neural differentiation base medium can include, but is not limited to E6 medium, as described herein and in U.S. Patent Publication No. 2014/0134732. In some embodiments, the neural differentiation medium to be used in the neural differentiation method is "E4" medium, which consists essentially of a base medium (e.g., DMEM/F12 or a similar base medium as described herein) containing water, salts, amino acids, vitamins, a carbon source, a buffering agent; plus selenium and insulin. Optionally, the neural differentiation medium to be used may also include ascorbate (referred to herein as an "E5" medium). In some embodiments, the neural differentiation medium to be used in the neural differentiation method is "E6" medium, which consists essentially of a carbonate-buffered E5 medium plus transferrin.

As used herein, the terms "E6 culture medium" and "E6" are used interchangeably and refer to a chemically defined culture medium comprising or consisting essentially of DF3S supplemented to further comprise insulin (20 μg/mL) and/or transferrin (10.67 ng/mL). The medium can be prepared based on the formula in previous publication (Chen et al., (2011) *Nature Methods.* 8(4), 424-429). Similar medium is available from Thermal Fisher/Life Technologies Inc. as Essential 6, or from Stem Cell Technologies as TeSR-E6. As used herein, the terms "E8 culture medium" and "E8" are used interchangeably and refer to a chemically defined culture medium comprising or consisting essentially of DF3 S supplemented by the addition of insulin (20 μg/mL), transferrin (10.67 ng/mL), human FGF2 (100 ng/mL), and human TGFβ1 (Transforming Growth Factor Beta 1) (1.75 ng/mL). The medium can be prepared based on the formula in previous publication (Chen et al., (2011) *Nature Methods.* 8(4), 424-429). As an alternative, the medium is also available from Thermal Fisher/Life Technologies Inc. as Essential 8, or from Stem Cell Technologies as TeSR-E8.

In other embodiments, the medium to be used includes at least the same components as a neural differentiation medium mentioned above, but the medium is substantially free of: a TGFβ superfamily agonist (e.g., Nodal); an albumin, and at least one of putrescine and progesterone. Optionally, a fibroblast growth factor (e.g., FGF2) may also be included in the medium to be used. In other embodiments, the medium to be used does not include a fibroblast growth factor. In some embodiments, a retinoic acid receptor agonist is also included to facilitate neural differentiation into certain neuronal lineages depending on the concentration of retinoid used. An exemplary class of suitable retinoic acid receptor agonists are the retinoids and retinoid analogs, which include without limitation All-Trans Retinoic Acid (ATRA), Retinol Acetate, EC23 (4-[2-(5,6,7,8-Tetrahydro-5,5,8,8-te-tramethyl-2-naphthalenyl)ethynyl)-benzoic acid; CAS No: 104561-41-3), BMS453 (4-[(1E)-2-(5,6-Dihydro-5,5-dimethyl-8-phenyl-2-naphthalenyl)ethenyl]-benzoic acid; CAS No: 166977-43-10), Fenretinide (N-(4-Hydroxyphenyl)retinamide; CAS No: 65646-68-6), AM580 (4-[(5,6,7,8-Tetrahydro-5,5,8,8-tetramethyl-2-naphthalenyl)carboxamido]benzoic acid; CAS No: 102121-60-8), Tazarotene (6-[2-(3,4-Dihydro-4,4-dimethyl-2H-1-benzothiopyran-6-yl)ethynyl]-3-pyridinecarboxylic acid ethyl ester; CAS No: 118292-40-3), and TTNPB (4-[(E)-2-(5,6,7,8-Tetrahydro-5,5,8,8-tetramethyl-2-naphthalenyl)-1-propenyl]benzoic acid; CAS No: 71441-28-6). Other exemplary retinoic receptor agonists that could be used include AC261066 (4-[4-(2-Butoxyethoxy-)-5-methyl-2-thiazolyl]-2-fluorobenzoic acid; CAS No: 870773-76-5), AC55649 (4'-Octyl-[1,1'-biphenyl]-4-carboxylic acid; CAS No: 59662-49-6), Adapalene (6-(4-Methoxy-3-tricyclo[3.3.1.13,7]dec-1-ylphenyl)-2-naphthalenecarboxylic acid; CAS No: 106685-40-9), AM80 (4-[[(5,6,7,8-Tetrahydro-5,5,8,8-tetramethyl-2-naphthalenyl)amino]carbonyl]benzoic acid; CAS No: 94497-51-5), BMS753 (4-[[(2,3-Dihydro-1,1,3,3-tetramethyl-2-oxo-1H-inden-5-yl)carbonyl]amino]benzoic acid; CAS No: 215307-86-1), BMS961 (3-Fluoro-4-[[2-hydroxy-2-(5,5,8,8-tetramethyl-5,6,7,8,-tetrahydro-2-naphthalenyl) acetyl]amino]-benzoic acid; CAS No: 185629-22-5), CD1530 (4-(6-Hydroxy-7-tricyclo[3.3.1.13,7]dec-1-yl-2-naphthalenyl)benzoic acid; CAS No: 107430-66-0), CD2314 (5-(5,6,7,8-Tetrahydro-5,5,8,8-tetramethyl-2-anthracenyl)-3-thiophenecarboxylic acid; CAS No: 170355-37-0), CD437 (6-(4-Hydroxy-3-tricyclo[3.3.1.13,7]dec-1-ylphenyl)-2-naphthalenecarboxylic acid; CAS No: 125316-60-1), and Ch55 (4-[(1E)-3-[3,5-bis(1,1-Dimethylethyl) phenyl]-3-oxo-1-propenyl]benzoic acid; CAS No: 110368-33-7). In some embodiments, the concentration of the retinoic acid receptor agonist (e.g., all-trans retinoic acid (ATRA) is about 0.1 μM to about 1.0 μM. A suitable concentration of retinoic acid receptor agonist ranges from about 0.1 μM to about 20 μM, e.g., about 0.2 μM, 0.3 μM, 0.5 μM, 1.0 μM, 2.5 μM, 3.0 μM, 3.5 μM, 4.0 μM, 5 μM, 7 μM, 10 μM, 12 μM, 15 μM, 17 μM or another concentration of ATRA from about 0.1 μM, to about 20 μM. In some embodiments, the concentration of ATRA is about 3.0 μM.

Guidance for directed differentiation of pluripotent stem cells to neural stem cells can be found in U.S. application Ser. No. 13/795,485 entitled "Simplified Compositions and Methods of Generating Neural Stem Cells from Human Pluripotent Stem Cells", U.S. application Ser. No. 14/496,796 entitled "Compositions and Methods for Precise Patterning of Posterior Neuroectoderm from Human Pluripotent Stem Cells" and U.S. application Ser. No. 16/044,236 entitled "Methods And Culture Substrates For Controlled Induction Of Biomimetic Neural Tissues Comprising Singular Rosette Structures" the contents of which are incorporated by reference in its entirety.

Suitable progenitor cells and culture conditions are contemplated that are able to form engineered cardiac tubes or gut epithelial tubes. For example, cardiac progenitors or gut epithelial progenitor cells may be seeded into the channels as described above.

Figure 9:
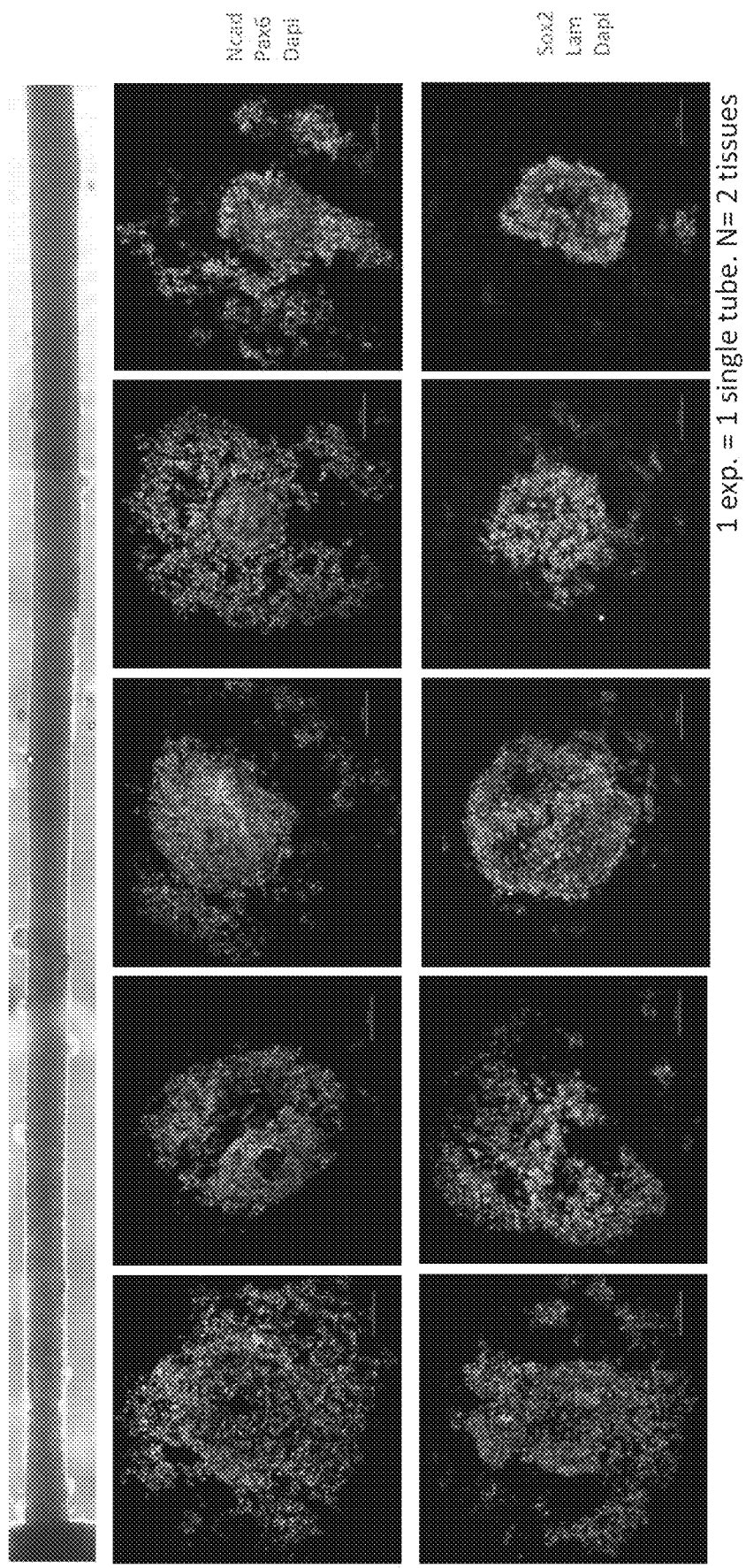
FIG. 9 shows staining of an in vitro biomimetic neuroepithelial tube with N-cad, Pax6, Sox2, Lam, and DAPI.

The resulting biomimetic 3D organoids made by the methods of the present invention have microscale cellular organization similar to that of the corresponding in vivo developing organ. For example, for an engineered 3D neuroepithelial tube, the biomimetic 3D organoids have a contiguous, polarized neural rosette structure (e.g., as demonstrated by laminin and N-cadherin polarized staining within the neuroepithelial tube) extending, in some cases, to 75% of the organoid's length. In some cases, the contiguous, polarized neural rosette structure extends at least 75%, 80%, 90%, or 99% of the organoid's length. As used herein, the term "polarized" refers to cells having bipolar (or tripolar or greater) morphology in which certain cellular components distributed unevenly between the two (e.g., apical and basal poles) or more poles of a cell. In some cases, a polarized cell is a neuroepithelial cell exhibiting apico-basal polarity with respect to expression of N-cadherin. For example, the presence of apico-basal polarity of N-cadherin foci is a surrogate marker of neural rosette formation. Polarized neural epithelial tissue is characterized by the presence of a coherent N-cadherin ring structure (formed by apical localization of N-cadherin) toward the hollow center of the neuroepithelial tube and laminin, a basement membrane protein, surrounding the neuroepithelial tube on the exterior surface, contacting the hydrogel. The images in FIG. 9 illustrate various polarized morphologies of engineered 3D neuroepithelial tubes prepared according to the methods of this disclosure.

The methods provided herein are in vitro methods for efficiently and robustly producing engineered biomimetic 3D neuroepithelial tubes having a singular rosette structure throughout the tube (as seen in the cross-section of the tube), where the engineered biomimetic 3D neuroepithelial tube exhibits microscale cellular organization (i.e., cytoarchitecture) similar to that of the developing human neuroepithelial tube. The term "biomimetic," as used in connection with an engineered 3D neuroepithelial tube refers to a singular tubular, or substantially tubular, structure throughout the channel within the hydrogel having similar structure to the anatomic structure and cytoarchitecture of the embryonic neuroepithelial tube in vivo (e.g., neural rosette-like cross-sectional structure). Biomimetic 3D neuroepithelial tubes described herein are in vitro-derived (e.g., engineered) tubes that mimic the polarized neural cytoarchitecture, with polarized NSCs displaying apical N-cadherin expression and basal extracellular matrix protein deposition of an embryonic neuroepithelial tube (FIG. 9). As used herein, the term "substantially tubular" means that the structure has an overall tubular configuration but need not be a perfect cylinder. In some cases, the structure has an overall tubular configuration that has an oval or circular shape in cross-section.

In some examples, the methods preferably yield a singular engineered biomimetic 3D neuroepithelial tube organoid exhibiting a polarized rosette-like cross-sectional structure in which at least 60% of cells of a cross-section of the polarized rosette structure are Pax6+/N-cadherin+ neuroepithelial cells, wherein greater than about 75% of the engineered biomimetic 3D neuroepithelial tube exhibits a singular rosette structure comparable to a developing human neuroepithelial tube.

In some embodiments, a hPSC-seeded hydrogel is cultured in the presence of one of the neural differentiation media described herein to obtain a population of cells that is at least about 60% PAX6-positive (by protein expression) within a period of at least about four days to about 16 days, e.g., about 4 days, 5 days, 6 days, 7 days, 8 days, 9 days, 10 days, 11 days, 12 days, 13 days, 14 days, or another period from at least about 4 days to about 16 days. In some embodiments, the cultured cells are at least 60% PAX6-positive at any period from about 8 days to about 16 days after initiating neural differentiation of the hPSCs.

The expression (or lack thereof) of a number of cell type-associated markers can be used to characterize the differentiation of hPSCs or NMPs into neural stem cells over the course of the methods described herein. For example, the expression of some markers associated with pluripotency in hPSCs decline over the course of differentiation of the hPSCs into neural stem cells. Such pluripotency markers include Oct4, Nanog, SSEA-3, SSEA-4, TRA-1-60, and TRA-1-81. Neuromesodermal progenitors (NMPs) have the following expression profile: SOX2+/OCT4-/T+/PAX6. During differentiation of NMPs to neural stem cells or neuronal cell types, expression of these NMP markers and other markers associated with mesoderm or endoderm also decline over time or are absent, e.g., T (Brachyury) and Sox 17. Conversely the expression of markers associated with neural stem cells increases over the course of differentiation. Suitable markers (at the RNA or protein level) for neural stem cells and neural differentiation include, but are not limited to, PAX6, SOX2, Nestin, N-Cadherin, and SOX1. Any appropriate method or methods can be used to confirm uniformity or the presence or absence of certain components in a biomimetic 3D organoid provided herein. Suitable methods for detecting the presence or absence of biological markers are well known in the art and include, without limitation, immunohistochemistry, qRT-PCR, RNA sequencing, and the like for evaluating gene expression at the RNA level. In some cases, methods such as immunohistochemistry are used to detect and identify cell types or biomolecules within a biomimetic 3D organoid. For example, whole organoids or portions thereof can be stained for specific differentiation markers by immunohistochemistry. In some cases, it will be advantageous to perform dual-label immunofluorescence to assess the relative expression of individual marker proteins or to detect multiple progenitor or differentiated cell types within a construct. Appropriate primary and secondary antibodies are known and available to those practicing in the art. In addition, microarray technology or nucleic acid sequencing (e.g., RNA sequencing) can be used to obtain gene expression profiles for biomimetic 3D organoids of the invention. Biological markers for neuroepithelial cells include, for example, Pax6 and N-cadherin. Quantitative methods for evaluating expression of markers at the protein level are also known in the art. For example, flow cytometry is used to determine the fraction of cells in a given cell population that express or do not express biological markers of interest.

In some cases, it will be advantageous to fix or freeze biomimetic 3D organoids of the invention for histology or microscopy. For example, biomimetic 3D organoids can be fixed in formalin or paraformaldehyde for plastic embedment and sectioning using routine methods. Alternatively, the tissues can be cleared to make the transparent and more amenable to imaging using light-based microscopy. In particular, light-sheet imaging and scanning electron microscopy (SEM) is useful to detect and analyze polarization within the engineered tube. In exemplary embodiments, confocal or light-sheet microscopy can reveal the distribution of cell types throughout a biomimetic 3D organoid of the invention. In some cases, a three-dimensional assembly of images obtained by confocal or light-sheet microscopy is used to analyze the distribution and organization of various cells and structures.

Induced pluripotent stem cell-derived engineered biomimetic 3D neuroepithelial tubes allow for modeling of drug responses in 3D structures that recapitulate neural development in an individual having, for example, a particular genetic background or detectable phenotype. Accordingly, subject-specific human iPS cell-derived biomimetic 3D neuroepithelial tubes are useful to identify genetic factors and epigenetic influences that contribute to variable effects of a known or unknown drug on neural development/neural differentiation.

Patient-specific somatic cells for reprogramming into induced pluripotent stem cells can be obtained or isolated from a target tissue of interest by biopsy or other tissue sampling methods. In some cases, subject-specific cells are manipulated in vitro prior to use in a three-dimensional tissue construct of the invention. For example, subject-specific cells can be expanded, differentiated, genetically modified, contacted to polypeptides, nucleic acids, or other factors, cryo-preserved, or otherwise modified prior to introduction to a hydrogel channel to obtain engineered biomimetic 3D neuroepithelial tubes described herein.

As used herein, the terms "chemically defined medium" and "chemically defined cultured medium" also refer to a culture medium containing formulations of fully disclosed or identifiable ingredients, the precise quantities of which are known or identifiable and can be controlled individually. As such, a culture medium is not chemically defined if (1) the chemical and structural identity of all medium ingredients is not known, (2) the medium contains unknown quantities of any ingredients, or (3) both. Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions. As used herein, the term "serum-free" refers to cell culture materials that are free of or substantially free of serum obtained from animal (e.g., fetal bovine) blood. In general, culturing cells or tissues in the absence of animal-derived materials (i.e., under conditions free of xenogeneic material) reduces or eliminates the potential for cross-species viral or prion transmission.

In a further aspect, provided herein is a method of generating an engineered biomimetic 3D neuroepithelial tube comprising along its entire length polarized neural cells which mimic the in vivo neuroepithelial tube formation. In some cases, the method comprises culturing the cell-seeded hydrogel into an engineered biomimetic 3D neuroepithelial tube having a singular rosette structure along its entire length. In further cases, the in vitro engineered biomimetic 3D neuroepithelial tube is cultured under conditions that promote further differentiation of cells of the engineered 3D neuroepithelial tube into various cell types of the human central nervous system. For example, the cell-seeded hydrogel can be cultured under conditions that promote differentiation of the stem cells into different types of neurons and neuron-supporting cells.

Any appropriate method can be used to analyze engineered biomimetic 3D neuroepithelial tubes structure. In preferred embodiments, the analysis method(s) are useful to detect the presence and identity of neurons and neuron-supporting cells (e.g., glia) in a biomimetic 3D neuroepithelial tube. For example, confocal microscopy and other microscopy-based imaging methods can be used. In such cases, confocal microscopy can be used to collect multiple images of cross-sections of the engineered 3D organoid or 3D neuroepithelial tube that have been treated with detectably labeled antibodies or stains having specificity for various cell types present at particular stages of development of the human neural tube. As described in the Examples that follow, confocal images can be obtained of cross-sections of the neuroepithelial tube fluorescently labeled to detect N-cadherin expression. For example, an exemplary protocol for detecting and analyzing neuroepithelial tube organization includes acquiring a series of confocal images using a 60× objective at 1024×1024 pixels to scan through the tissue in user-defined increments or steps, and analyzing a stack of the acquired confocal images to detect cell types present in or adjacent to the cellular structures using, for example, a machine learning program for image classification.

An engineered in vitro biomimetic 3D organoid structure encapsulated by a hydrogel made by the methods described herein is also contemplated. In one example, the engineered biomimetic 3D organoid structure is an engineered biomimetic 3D neuroepithelial tube comprising polarized neuronal cells within the hydrogel channel.

Hydrogels comprising channels suitable for producing biomimetic 3D organoid structures are also contemplated to be obtained by the methods described herein.

The hydrogel is configured to promote neural differentiation and morphogenesis of human pluripotent stem cells cultured within the channel of the hydrogel to form an engineered biomimetic 3D organoid, e.g., an engineered 3D neuroepithelial tube.

In another aspect, provided herein are three-dimensional (3D) preparations of engineered biomimetic neuroepithelial tubes comprising, preferably, a single rosette structure throughout the length of the hydrogel channel or a portion thereof. In some cases, the three-dimensional preparations are in vitro organoids comprising polarized Pax6+/N-cadherin+ neural stem cells (NSCs) in a biomimetic 3D neuroepithelial tube. In some embodiments, the in vitro 3D neuroepithelial tube comprises a single ring of polarized Pax6+/N-cadherin+ NSCs mimetic of the developing neuroepithelial tube along the length of the channel (as seen by in a cross-section of the channel), or a portion thereof. Applications of in vitro engineered 3D neuroepithelial tube provided herein include, without limitation, in vitro screening of agents for those that modulate neuroepithelial tube or CNS development. For example, in vitro-derived biomimetic 3D neuroepithelial tubes can be used for high throughput screening of candidate agents.

In another aspect, provided herein is an engineered biomimetic 3D neuroepithelial tube having cellular architecture (as seen by in a cross-section of the tube) analogous to developing neuroepithelial tube slice cultures. In particular, provided herein is biomimetic 3D neuroepithelial tubes that provide an engineered, standardized model of the developing human CNS, in whole or in part. As described herein, hydrogels containing a channel are used to reproducibly obtain biomimetic 3D neuroepithelial tubes comprising a singular neural structure and to further differentiate cells within the biomimetic 3D neuroepithelial tube.

The cell-seeded hydrogels as described herein allow unprecedented control of 3D neuroepithelial stem cell tissue morphogenesis, which the current state-of-the-art methods lack. This discovery represents a significant advancement and universal basis for engineering anatomically biomimetic in vitro tissues that recapitulate stages of human CNS development. Standardized production of such biomimetic in vitro 3D tissues provide a revolutionary experimental paradigm for conducting personalized neuroscience studies. For example, neuroepithelial organoid tissues are useful to study the effects of genetic mutations on development and function across the human CNS, to conduct personalized neuroscience studies using neural stem cells derived from induced pluripotent stem cells (iPS cells) of a particular human subject, and to assess neurotoxicity of various agents or other effects on neural development. In some cases, engineered 3D neuroepithelial tubes of the invention are useful in drug discovery and development including screening for metabolic stability, drug-drug interactions, toxicity and infectious disease. Exemplary test agents include, without limitation, infectious agents, proteins, peptides, antibodies, small molecules, oligonucleotides, polynucleotides, peptidomimetics, cytotoxic agents, pharmaceutical agents, and xenobiotics (e.g., environmental toxin, chemical/biological warfare agent, a natural compound, and a nutraceutical).

In some cases, engineered biomimetic 3D neuroepithelial tubes as described herein can be screened to identify agents that modulate neural tube development and development of the human CNS. Screening methods can comprise or consist essentially of (a) contacting a test agent to in vitro derived biomimetic 3D neuroepithelial tubes; and (b) detecting an effect of the agent on biomimetic 3D neuroepithelial tubes (e.g., disrupt or otherwise alter development of the neuroepithelial tube or differentiation of neural cell types within the engineered 3D neuroepithelial tube). In some cases, screening methods include screening candidate compounds to identify test agents that promote the development of the human CNS. In other cases, candidate compounds can be screened for toxicity to human neural cell types or tissues. In some cases, detecting comprises detecting at least one positive or negative effect of the agent on morphology or life span of such cells and tissues, whereby an agent that increases or reduces the life span of human neural cell types or tissues, or has a positive or negative impact on the morphology of human neural cell types or tissues, is identified as having an effect on development of the human neuroepithelial tube or neural tissues. In some cases, detecting comprises performing a method selected from the group consisting of RNA sequencing, gene expression profiling, transcriptome analysis, cell proliferation assays, metabolome analysis, detecting reporter or sensor, protein expression profiling, Forster resonance energy transfer (FRET), metabolic profiling, and microdialysis. In some cases, the agent can be screened for an effect on gene expression, and detecting can comprise assaying for differential gene expression relative to an uncontacted biomimetic 3D neuroepithelial tubes. In addition, in some cases, 3D neuroepithelial tubes of this disclosure are suitable as direct transplants for tissue regeneration and repair.

In exemplary embodiments, detecting and/or measuring a positive or negative change in a level of expression of at least one gene following exposure (e.g., contacting) of a test compound to one or more biomimetic 3D neuroepithelial tubes comprises whole transcriptome analysis using, for example, RNA sequencing. In such cases, gene expression is calculated using, for example, data processing software programs such as Light Cycle, RSEM (RNA-Seq by Expectation-Maximization), Excel, and Prism. See Stewart et al., *PLoS Comput. Biol.* 9:e1002936 (2013). Where appropriate, statistical comparisons can be made using ANOVA analyses, analysis of variance with Bonferroni correction, or two-tailed Student's t-test, where values are determined to be significant at $P<0.05$. Any appropriate method can be used to isolate RNA or protein from neural constructs. For example, total RNA can be isolated and reverse transcribed to obtain cDNA for sequencing.

Test compounds can be dissolved in a solvent such as, for example, dimethyl sulfoxide (DMSO) prior to contacting to one or more biomimetic 3D neuroepithelial tubes provided herein. In some cases, identifying agents comprises analyzing the contacted biomimetic 3D neuroepithelial tubes for positive or negative changes in biological activities including, without limitation, gene expression, protein expression, cell viability, and cell proliferation. For example, microarray methods can be used to analyze gene expression profiles prior to, during, or following contacting the plurality of test compounds to the biomimetic 3D neuroepithelial tubes. In some cases, a method of the present invention further comprises additional analyses such as metabolic assays and protein expression profiling.

In another aspect, provided herein is a kit comprising one or more components useful for obtaining an in vitro 3D neuroepithelial tube organoid. Components of the kit can include one or more hydrogel containing a channel as described herein. The kit can also contain a chemically defined culture medium and one or more medium additives. The kit may further contain progenitor cells useful for the seeding of the channel and instructions for cell seeding and culture. In another aspect, provided herein is a kit comprising one or more components useful to prepare a 3D model of the developing human neuroepithelial tube according to the methods provided herein. Components of the kit can include one or more hydrogel comprising a channel and one or more progenitor cells.

The invention will be more fully understood upon consideration of the following non-limiting Examples.

EXAMPLES

Example 1—Formation of Hydrogels for Producing 3D Engineered Neuroepithelial Tubes This Example demonstrates the production of a biocompatible hydrogel capable of forming a 3D engineered neuroepithelial tube. FIG. 1 depicts a method of making hydrogels with tube like shapes in which stem cells can be injected and subsequently form a neuroepithelial tube organoid. Engineering approaches as described in U.S. Patent Publication No. US2017/0157802 were modified to design and produce hydrogels with tube-like shapes throughout the length in which stem cells can be injected and subsequently form a 3D engineered neural tube structure. As depicted in FIG. 1, a tube shape material (e.g., sacrificial material) was selected, in this example fishing line or a polyvinyl alcohol (PVOH), which is made by injection molding and is a water soluble material. The sacrificial material (e.g., fishing line) was immobilized within a casting chamber (FIG. 10) using holding needles and a hydrogel, e.g., an alginate hydrogel, was cast around the sacrificial material (e.g., by introducing into the casting chamber a volume of hydrogel polymer solution sufficient to surround the sacrificial template). The hydrogel polymer solution is contacted with a crosslinking solution (e.g., divalent cation solution) in a sufficient amount to crosslinked the hydrogel polymer in the solution to form a hydrogel shell surrounding the sacrificial template. The sacrificial template is then removed by sliding the fishing line out of the hydrogel after it has cured, leaving an open channel.

Figure 10:
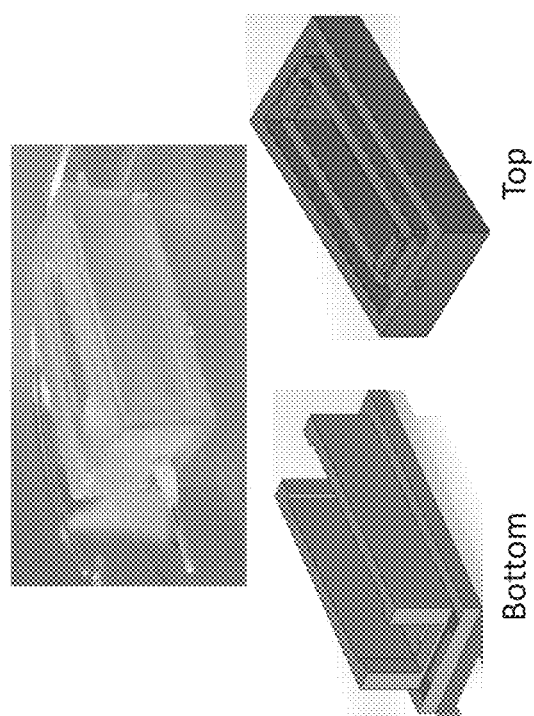
FIG. 10 is an exemplary device used to make the hydrogels in the present invention comprising a 2-piece mold made from biocompatible dental resin that is autoclavable. Top well piece designed for pipetting alginate pre-hydrogel solution into the mold and precisely orienting gel loading tips (~300 μm ID), which hold the tube molding material (e.g., nylon fishing line or PVOH sacrificial mold).
Figure 11:
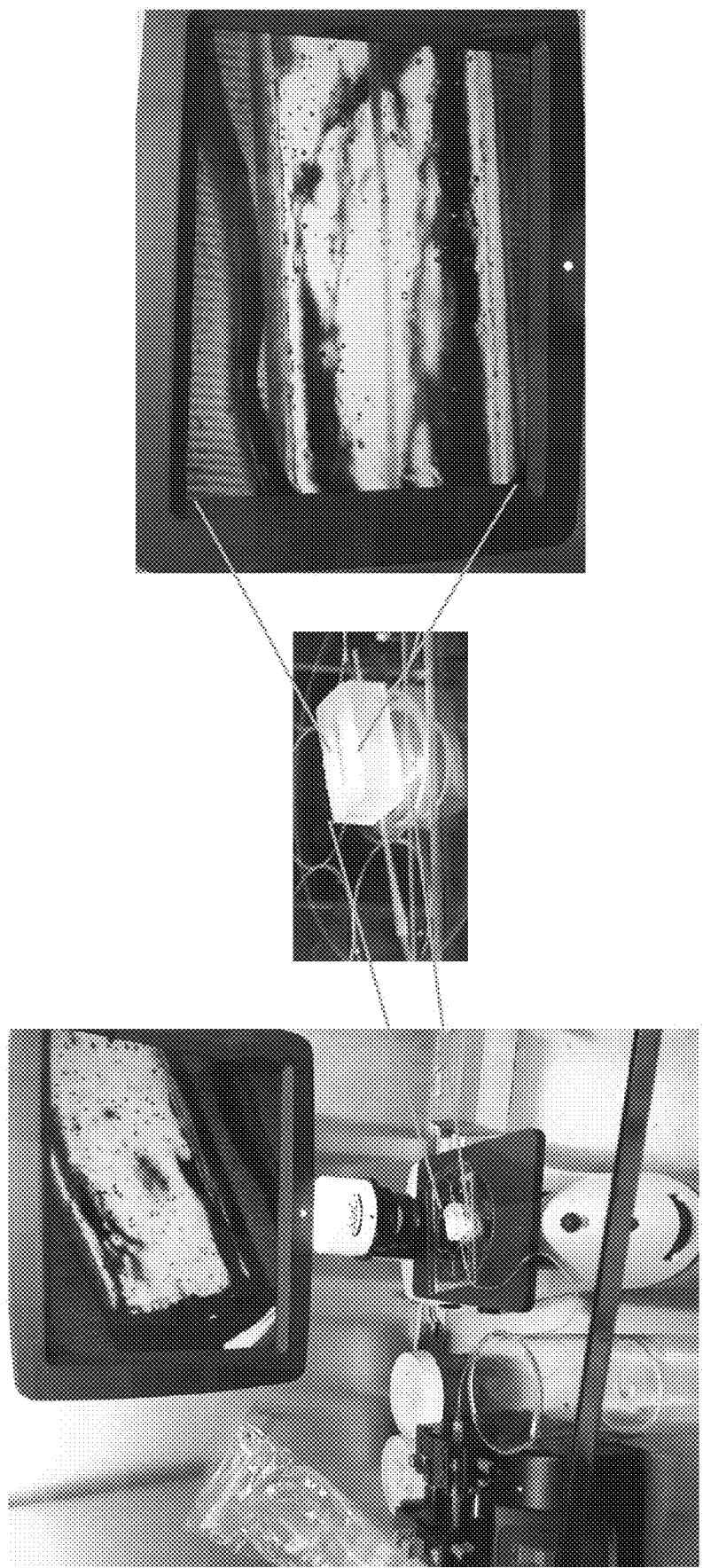
FIG. 11 depicts an exemplary injection setup which includes the device with the hydrogel, a syringe pump, and a microscope connected to a camera for close-up imaging during the injection process.

FIG. 10 demonstrates a device suitable for deriving the hydrogels. This is a 2-piece mold 3D printed using biocompatible dental resin that is autoclavable. Top well allows for pipetting alginate solution prior to hydrogel formation, as well as, holding gel loading tips (~300 μm ID) to spatially orient the tube molding material (e.g., fishing line or PVOH sacrificial material). A suitable injection set-up is depicted in FIG. 11. The depicted set-up includes the device with the hydrogel, a syringe pump, and a microscope connected to a camera for close-up imaging during the injection process.

In order to maintain the cells within the hydrogel chamber, the second end of the hydrogel channel is sealed or closed as depicted in FIG. 2 before the channel is seeded with cells. The channel-containing alginate hydrogel end is dipped in a chelator, e.g., EDTA at 50 μM for about 10 minutes. The hydrogel end is then transferred to an alginate solution for about 1 minute and then transferred to a divalent cation solution (e.g., 2% (w/v) $CaCl_2$ solution) for about 20 minutes in order to form a layer of alginate on the second end of the hydrogel. The resultant hydrogel now has only a first open end in which to inject cells. The second sealed end is sealed with a sufficient layer of alginate to retain the injected cells within the channel but to allow for flow of excess medium through the closed end of the channel, thus allowing for cells to be densely packed within the channel (FIG. 3).

Example 2: Production of Biomimetic 3D Engineered Neuroepithelial Tubes

This Example provides a method of forming 3D neuroepithelial tube organoids having 3D structure similar to the developing primordial neural tube in vivo. Additional methods and results related to the assays described below, including discussion of poly(vinyl alcohol)-calcium salt sacrificial templates, are described by McNulty et al., *Acta Biomaterialia*, 95:258-268 (2019).

Human pluripotent stem cell derived organoids have revolutionized the ability to model developmental morphogenesis in vitro. However, standard organoid derivation protocols initiate using a microscale spheroidal cell aggregate morphology, which is achieved upon spontaneous aggregation of cell suspensions but is not mimetic of many tissue-specific developmental processes (Lancaster et al., *Science*, 345 (2014), Marti-Figueroa & Ashton, *Acta Biomater.*, (2017) 54:35-44). To demonstrate an organoid engineering application of alginate hydrogels sacrificially molded using PVOH-Ca($C_2H_3O_2$)$_2$ micro-fiber templates, we investigated the use of this platform to engineer neuroepithelial organoids of microscale cylindrical morphology, which is mimetic to the embryonic neural tube that gives rise to all central nervous system tissues.

Figures 4A, 4B:
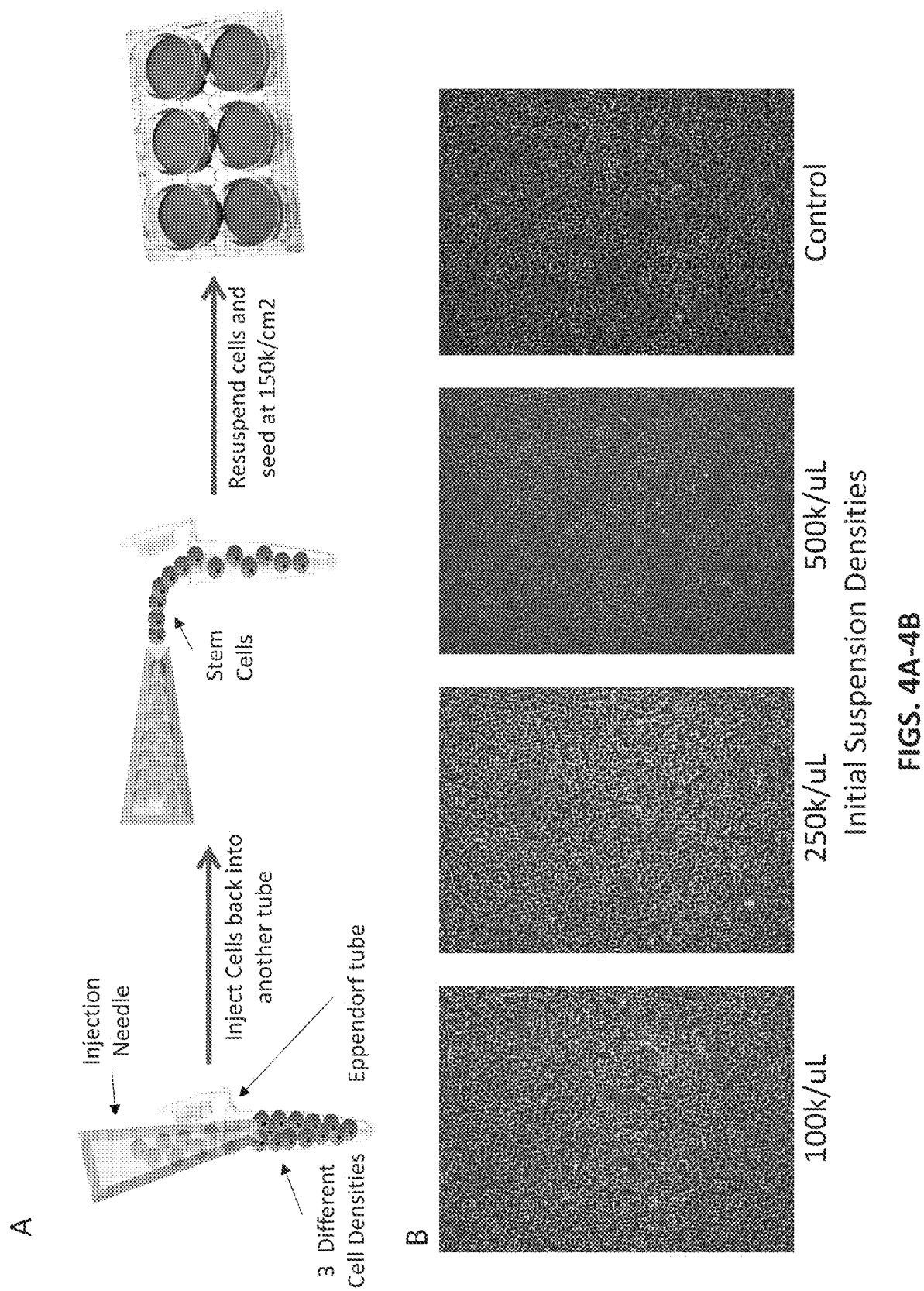
FIGS. 4A-4B depict an embodiment of the method and testing of cell injection density. Panel (A) depicts a schematic of the method used to test the optimal suspension density for injection into the hydrogels. Panel (B) provides representative figures of the cell densities after undergoing injection to allow for determining the optimal cell density to seed hydrogels with low cell death.

For successful contiguous aggregate formation within sacrificially molded alginate hydrogels, it was hypothesized that high concentration cell slurry injections into the hydrogel's molded, microscale channel is required. Thus, it was investigated which H9 hESC cell slurry concentrations could be injected through a gel-loading micropipette tip without decreasing cell viability due to shear stress (FIG. 4A). Cell suspensions of 100,000, 250,000, and 500,000 cells/µL concentrations were prepared, collected and injected by syringe pump through a gel-loading micropipette tip, and re-seeded back into MATRIGEL™-coated 6-well plates at a 150,000 cells/cm² density. Observation of the cell density 24 hours (hrs) post-seeding indicated that cell slurries up to 250,000 cells/µL preserved cell viability and survival at levels comparable to the positive control which used a standard cell subculturing protocol (FIG. 4B). Based on this result, the 250,000 cells/L cell slurry concentration was used for injections in subsequent neuroepithelial organoid formation experiments.

Figures 5A, 5B, 5C, 5D, 5E:
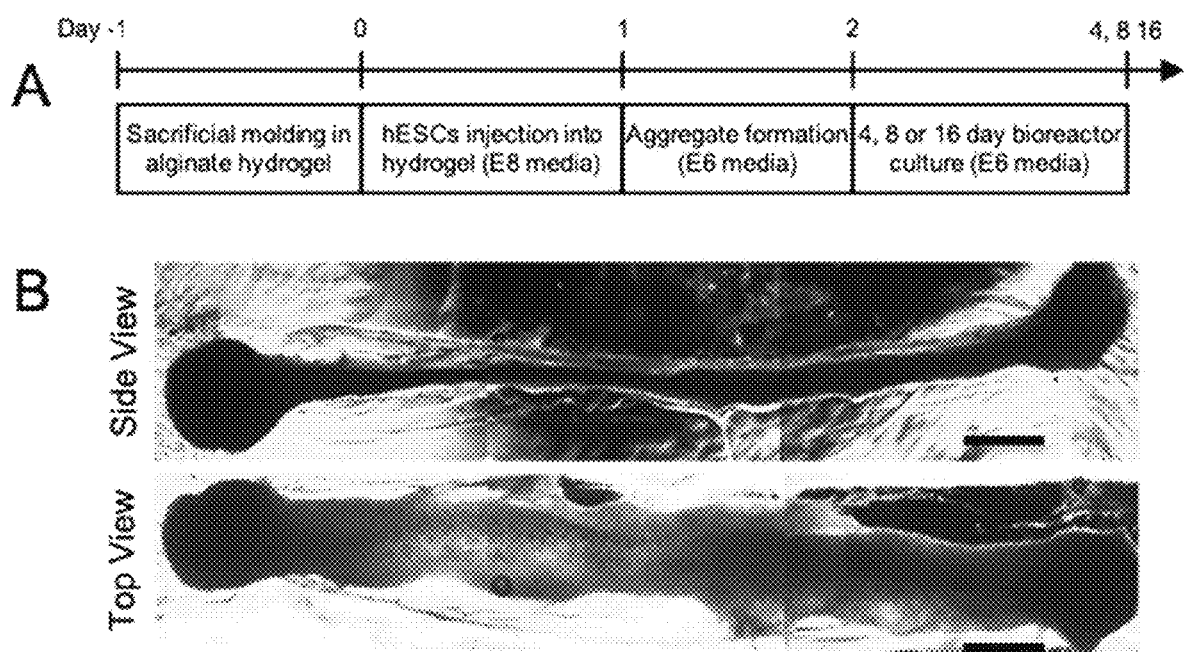
FIGS. 5A-5E demonstrate producing engineered neuroepithelial organoids using sacrificially molded alginate hydrogels. (A) Experimental timeline of neuroepithelial organoid derivation. Alginate hydrogels were prepared the day before injection. (B) Brightfield image of organoids after 16 days of culture demonstrating their elliptical morphology. (C) Quantification of organoid dimensions after 4, 8, and 16 days of bioreactor culture (n=5 organoids). The PVOH-Ca($C_2H_3O_2$)$_2$ template dimensions were measured before sacrificial hydrogel molding. (D) Immunocytochemistry of neuroepithelial organoid cryosections for basement membrane protein Laminin (Lam) and NEC polarization marker N-cadherin (Ncad) after 4, 8, and 16 days of bioreactor culture. (E) Quantification of the average number N-cadherin+ polarization foci (left) and rosettes per cryosection (middle) and the average rosette diameter (right). Data was acquired from two organoids per day, and ~8 (Day 4), ~13 (Day 8), and ~4 (Day 16) cryosections per organoid. Error bars represent standard deviation; *$P<0.05$, One-way ANOVA with post-hoc Tukey-Kramer test. Scale bars are (B) 500 and (D) 100 μm.
Figure 6:
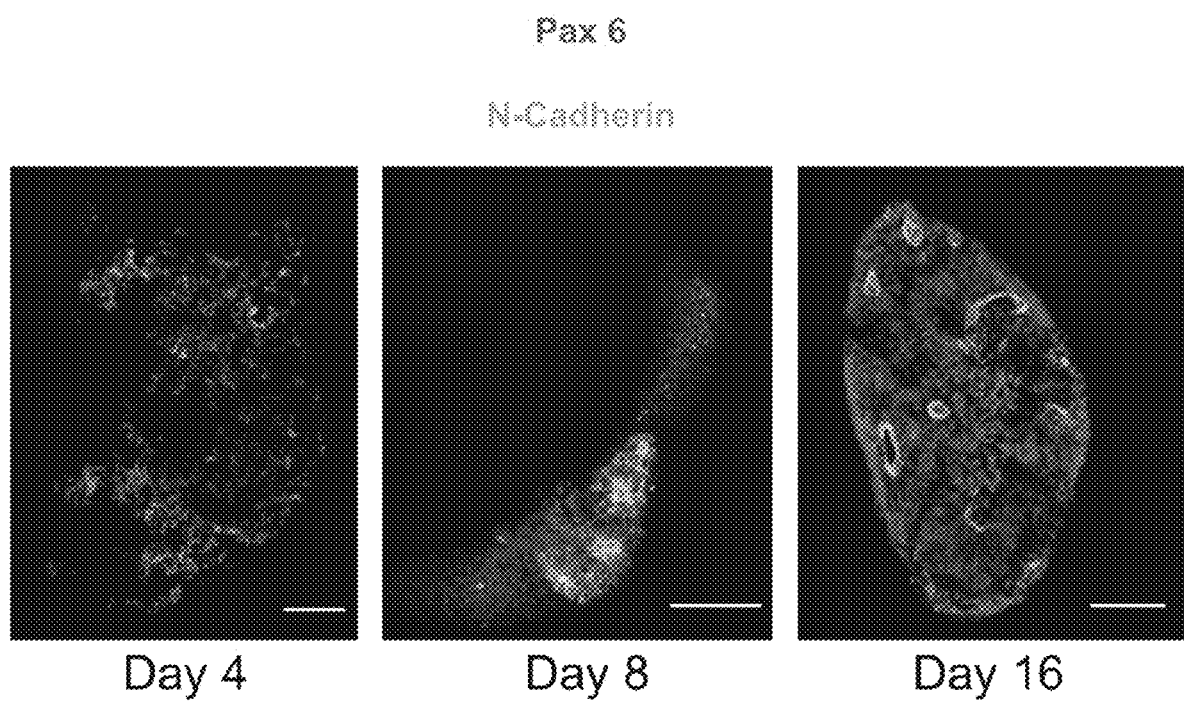
FIG. 6 presents representative images of immunocytochemical staining of neuroepithelial organoid cryosections for Pax6 (red) and N-cadherin (green). Scale bars are 100 m.

In order to mimic the germinal neuroepithelial tube's tubular morphology, PVOH-Ca($C_2H_3O_2$)$_2$ fiber templates with an elliptical cross-section of ~300×600 µm minor and major axes were used to sacrificially mold alginate hydrogels. H9 hESCs were injected into the alginate hydrogels' sacrificially molded channel, cultured for 24 hrs in static well plate culture, and transferred to stirred tank bioreactor culture for up to 15 additional days (FIGS. 5A and 5B). Cylindrical cell aggregate morphology and morphogenesis were analyzed at 4, 8, and 16 days of culture. In comparison to the initial PVOH-Ca($C_2H_3O_2$)$_2$ templates, the morphing aggregates' dimensions never exceed that of the template, and in many cases, appeared to contract to dimensions smaller than the molded channels over the culture period (FIGS. 5B and 5C). Formation of polarized rings by Pax6+ NECs, a.k.a. neural rosettes (Lippmann et al., *Stem Cells*, 32 (2014), pp. 1032-1042) with apical N-Cadherin+ polarization and basal laminin deposition were observed by both Day 8 and 16 of bioreactor culture but largely absent at Day 4 (FIG. 5D and FIG. 12). At Day 4, primarily small foci of N-Cadherin+ polarization we observed, and as the bioreactor culture proceeded through Day 16, the number of N-Cadherin+ polarization foci decreased significantly while both the number and size neural rosettes increased significantly (FIG. 5E).

As the ring formations frequently had diameters of approximately 200-250 µm, the method was performed again with a channel having a diameter of 250 µm using 250 µm fishing line as the sacrificial template. The cells again were stained at day 16 with N-cadherin, laminin and DAPI showing the organization of the neuroepithelial tube having polarization. As demonstrated in FIG. 9, the engineered 3D neuroepithelial tube expresses the markers for neuronal cells, e.g. Pax6 and Sox2, along with basal laminin expression and apical N-cadherin expression. FIGS. 7A and 7B provide further examples, showing the reproducibility of the ability to form 250 µm in vitro derived engineered 3D neuroepithelial tubes, although the expression of laminin and N-cadherin reveal that the engineered tube (FIG. 7B, right images) is inverted relative to an endogenous neural tube (FIG. 7B, left image).

Figure 8:
FIG. 8 shows exemplary photos of the injection site and sealed portion over injection site in the hydrogel model. Red boxes and circles highlight the new hydrogel formed around the initial hydrogel ends indicated by the blue boxes and circles. The star shows cells that have been injected prior to hydrogel sealing.

The cell-seeded hydrogels are encapsulated in alginate hydrogel in order to retain the cells within the channel while culturing in the spinner flask. As shown in FIG. 8, different thicknesses of the seal over the injection site can be obtained depending on the time the hydrogel is submerged in the divalent cation solution (using the method as depicted in FIG. 3). Red boxes and circles highlight the new hydrogel formed around the initial hydrogel ends in blue boxes and circles. The star shows cells that have been injected prior to hydrogel encapsulation.

Together, these results demonstrate that PVOH-Ca ($C_2H_3O_2$)$_2$ template-molded alginate hydrogels can be used to engineer neuroepithelial organoids, the initial phase of neural organoid derivation (Lancaster et al., *Nature*, 501 (2013), pp. 373-379), with a biomimetic, microscale cylindrical versus spheroidal morphology. Moreover, the organoids continue to develop while cultured within alginate hydrogel molds. While these data demonstrate the platform's utility for hESC-derived neural organoid engineering, it is expected to be highly useful for diverse tissue engineering and advanced biomanufacturing applications.

Materials and Methods

Hydrogel Imaging and Reconstruction:

Hydrogels were imaged using standard photography or a MicroCATII (Siemens AG.) at the University of Wisconsin Carbone Cancer Center's small animal imaging facility. The Digital Imaging and Communications in Medicine (DICOM) image stacks were then reconstructed and converted into STL graphic bodies using Mimics software (Materialize NV.). Image analysis was performed using a combination of Magics (Materialize NV.), MeshLabs, and Solidworks (Dassault Systemes).

Neuroepithelial Cell Derivation:

WA09 (H9, WiCell) human embryonic stem cells (Passage 28-40) were maintained in the pluripotent state in E8 medium (Thermofisher) on MATRIGEL™-coated plates. The H9 line was authenticated as karyotypically normal by the provider and within 6 months of these experiments and tested for *mycoplasma* with negative results (WiCell). After banking, the cells were used for no more than 15 passages during experimentation. Neural induction was executed as previously described (Lippmann et al., *Stem Cells*, 32 (2014), pp. 1032-1042). Briefly, hESCs were passaged with Accutase (Life Technologies) onto MATRIGEL™-coated plates at a density of 1×10⁵ cells/cm² with 10 mM ROCK inhibitor (Y27632; R&D Systems). The following day, cells were changed to E6 medium (ThermoFisher) for 4 days with daily, complete media changes.

Formation of Organoids in Alginate Hydrogel Channels:

Neuroepithelial cells (NECs) were washed with 2 mL PBS, accutased for 5 min, and removed from the surface by gentle pipetting. After collection by centrifugation, cells were gently resuspended at a concentration of 250,000 cells/µL in E8 medium containing 10 µLM ROCK inhibitor Y27632 and 1:200 Penicillin-Streptomycin (Penstrep, 10,000 U/mL) (Invitrogen). Using a PHD Ultra™ syringe pump (Harvard Apparatus) loaded with a 3 cc syringe connected via tubing to a 1-200 µL gel-loading pipette tip (VWR, Cat. No. 37001-150), the cells were collected and injected into the alginate hydrogel's molded channel at a rate of 5-50 nL/second in a sterile environment. The injection process was visualized using an EVOS™ XL Core Imaging System (ThermoFisher). After injection, the hydrogels were removed from their stainless steel devices and cultured in E8 media in 6-well plates for the first 24 hrs. Then, they were transferred to a sterile 125 mL Pyrex Spinner flask (ThermoFisher) agitated on an orbital shaker (Scilogex, Cat. No. SK-0330-Pro) for an additional 4, 8, or 16 days in E6 medium containing 1:200 Penstrep. Complete media changes were conducted every third day.

Organoid Fixation and Immunohistochemistry:

After culture, hydrogels containing organoids were washed with PBS 3 times for 10 min, and subsequently fixed with paraformaldehyde (PFA) for 15 min. After fixation, hydrogels were transferred to a 30% sucrose-PBS solution for 1-3 days. Next, the organoids were removed from the hydrogels by incubation in a 100 mM EDTA solution for 1 hour, collected by gentle pipetting using a cut 1000 µL pipette tip, and embedded in OCT compound (Sigma-Aldrich) until sectioning. Organoids were sectioned as 30 µm thick slices onto Superfrost Plus microscope slides (ThermoFisher). The slides were washed 3 times with PBS to remove OCT, blocked with TBSDT (Tris Buffered Saline+ 5% Donkey Serum+0.3% Triton X), and incubated in primary antibodies against mouse-anti-N-Cadherin (BD Biosciences, Cat. No. 610920) and rabbit-anti-Pax6 (Biolegend, Cat. No. 901301), or mouse-anti-N-Cadherin and rabbit-anti-Laminin (Abcam, Cat. No. ab30320) for 3 days. All primary antibodies were used at a 1:200 dilution. After incubation, the slides were washed 5 times with TBST (TBS+0.3% Triton X) and incubated for 1 day in secondary antibodies Alexa 488® donkey-anti-mouse and Alexa 555® donkey-anti-rabbit (1:250, ThermoFisher) and stained with DAPI (Invitrogen, Cat. No. D1306) for 20 min prior to washing with TBS 5 times. Slides were mounted using Prolong Gold anti-fade (ThermoFisher) under No. 1 coverslips (ThermoFisher) and imaged using a Nikon AR1 confocal microscope.

Statistical Analysis: RStudio® was used to conduct all statistical analysis. Experimental replicates or number of groups are detailed in figure legends, and error bars show standard deviations. One-way ANOVAs with post-hoc Tukey-Kramer tests were conducted to determine statistical significance. P<0.05 was considered statistically significant.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. A method of preparing an engineered biomimetic 3D organoid in vitro, the method comprising:
   (a) providing a hydrogel having a channel therein, the channel having a first end and a second end;
   (b) sealing one or more of the first and second ends of the channel;
   (c) seeding the channel with human pluripotent stem cells (hPSCs),
   (d) contacting the hydrogel comprising the hPSC-seeded channel to an alginate solution, and then contacting the alginate-contacted hydrogel to a divalent cation solution, thereby producing a hPSC-seeded channel encapsulated in crosslinked hydrogel, and
   (e) culturing the encapsulated hPSC-seeded channel in a culture medium for about four (4) to about sixteen (16) days for the hPSCs within the channel to differentiate into neuroepithelial cells, whereby a biomimetic 3D organoid comprising polarized neuroepithelial cells and having microscale cellular organization similar to that of an in vivo developing human neural tube is obtained.

2. The method of claim 1, wherein the hydrogel is an alginate hydrogel.

3. The method of claim 1, wherein the divalent cation solution is a calcium chloride ($CaCl_2$) solution.

4. The method of claim 1, wherein sealing comprises contacting the first end or the second end of the channel to an alginate solution and contacting the alginate-contacted end to a divalent cation solution, thereby producing a channel comprising a sealed end and an unsealed end.

5. The method of claim 4, wherein seeding the channel comprises injecting a hPSC suspension having a cell density of about 500,000 cells/µl or less into the unsealed end.

6. The method of claim 1, wherein sealing comprises contacting the first end and the second end of the channel into an alginate solution and contacting each alginate-contacted end into a divalent cation solution, thereby producing a channel comprising a first sealed end and a second sealed end.

7. The method of claim 6, wherein seeding the channel comprises injecting a hPSC suspension having a cell density of about 500,000 cells/µl or less into the first sealed end or the second sealed end.

8. The method of claim 7, further comprising re-sealing the end into which the hPSC suspension is injected, wherein re-sealing comprises;
   contacting an alginate solution to the hPSC suspension-injected end; and
   contacting the alginate-contacted end to a divalent cation solution to cross-link the alginate, thereby producing a hPSC-seeded channel comprising a sealed end and a re-sealed end.

9. The method of claim 1, wherein the biomimetic 3D organoid is a biomimetic neuroepithelial organoid comprising polarized neural stem cells.

10. The method of claim 1, wherein the channel is substantially tubular.

11. The method of claim 10, wherein the diameter of the substantially tubular channel is between about 50 µm to about 700 µm.

12. The method of claim 10, wherein the diameter of the substantially tubular channel is between about 100 µm to about 300 µm.

13. The method of claim 1, wherein the culture medium is sufficient to promote the self-organization and spontaneous morphogenesis of the hPSCs into neuroepithelial organoids.

14. The method of claim 13, wherein the culture medium is a neural differentiation medium comprising water, salts, amino acids, vitamins, a carbon source, a buffering agent, selenium, ascorbate, insulin, transferrin, and a Rho kinase (ROCK) inhibitor.

15. The method of claim 14, wherein the hydrogel comprising the cell-seeded channel is cultured within a spinner flask containing the neural differentiation medium.

16. The method of claim 1, wherein the hydrogel is produced by the method comprising:
   (a) providing a sacrificial template of a predefined shape immobilized within a casting chamber,
   (b) introducing into the casting chamber a volume of hydrogel polymer solution sufficient to surround the sacrificial template, (c) contacting the hydrogel polymer with a cross-linking solution to form a hydrogel shell surrounding the sacrificial template, and
(d) removing the sacrificial template, thereby providing a hydrogel with a channel therein.

17. The method of claim 16, wherein the sacrificial template is a water soluble thermoplastic-divalent cationic salt composite material.

18. The method of claim 16, wherein the sacrificial template is poly(vinyl alcohol) material coated in divalent cations.

\* \* \* \* \*